(12) United States Patent
O'Shea et al.

(10) Patent No.: US 10,738,325 B2
(45) Date of Patent: *Aug. 11, 2020

(54) EXOGENOUS GENE EXPRESSION IN THERAPEUTIC ADENOVIRUS FOR MINIMAL IMPACT ON VIRAL KINETICS

(71) Applicant: Salk Institute for Biological Studies, La Jolla, CA (US)

(72) Inventors: Clodagh O'Shea, San Diego, CA (US); William Partlo, San Diego, CA (US); Colin Powers, San Diego, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/110,207

(22) Filed: Aug. 23, 2018

(65) Prior Publication Data

US 2018/0355379 A1 Dec. 13, 2018

Related U.S. Application Data

(63) Continuation of application No. PCT/US2017/019086, filed on Feb. 23, 2017.

(60) Provisional application No. 62/298,653, filed on Feb. 23, 2016.

(51) Int. Cl.
| | |
|---|---|
| *C12N 15/86* | (2006.01) |
| *C12N 7/00* | (2006.01) |
| *A61K 48/00* | (2006.01) |
| *A61K 39/00* | (2006.01) |
| *C12N 15/62* | (2006.01) |
| *C12N 15/63* | (2006.01) |

(52) U.S. Cl.
CPC .... *C12N 15/86* (2013.01); *C12N 2710/10011* (2013.01); *C12N 2710/10043* (2013.01); *C12N 2710/10051* (2013.01); *C12N 2840/00* (2013.01)

(58) Field of Classification Search
CPC .. A61K 2300/00; A61K 39/12; A61K 35/761; A61K 39/00; A61K 48/00; A61K 2039/5156; A61K 35/76; A61K 2039/70; A61K 39/235; C12N 15/86; C12N 2840/203; C12N 7/00; C12N 2710/10343; C12N 15/62; C12N 15/63; C12N 2710/10332; C12N 2710/10041; C12N 2710/10043; C12N 15/861; C12N 2710/00034; C12N 2710/00043; C12N 2710/10011; C12N 2710/10051; C12N 2710/10062; C12N 2840/00
See application file for complete search history.

(56) References Cited

U.S. PATENT DOCUMENTS

| | | |
|---|---|---|
| 2003/0143730 A1 | 7/2003 | Blanche et al. |
| 2004/0191761 A1 | 9/2004 | Routes |
| 2017/0035818 A1* | 2/2017 | Seymour .............. A61K 35/761 |

FOREIGN PATENT DOCUMENTS

| | | |
|---|---|---|
| WO | WO 2012/024351 | 2/2012 |
| WO | WO 2013/135615 | 9/2013 |
| WO | WO 2014/000026 | 1/2014 |
| WO | WO 2015/155370 | 10/2015 |
| WO | WO 2016/049201 | 3/2016 |
| WO | WO 2017/147265 | 8/2017 |

OTHER PUBLICATIONS

Funston GM, Kallioinen SE, de Felipe P, Ryan MD, Iggo RD. Expression of heterologous genes in oncolytic adenoviruses using picornaviral 2A sequences that trigger ribosome skipping. J Gen Virol. Feb. 2008;89(Pt 2):389-96.*
Funston et al., "Expression of Heterologous Genes in Oncolytic Adenoviruses using Picornaviral 2A Sequences that Trigger Ribosome Skipping," *J. Gen. Virol.*, vol. 89:389-396, 2008.
Ketzer et al., "Synthetic riboswitches for external regulation of genes transferred by replication-deficient and oncolytic adenoviruses," *Nucleic Acids Res* 40(21):e167 (10 pages), 2012.
Kim et al., "High Cleavage Efficiency of a 2A Peptide Derived from Porcine Teschovirus-1 in Human Cell Lines, Zebrafish and Mice," *PLoS One*, vol. 64:e18556, 2011.
Pelka et al., "Adenovirus E1A Directly Targets the E2F/DP-1 Complex," *J. Virol.*, vol. 85:8841-8851, 2011.
Szymczak et al., "Correction of Multi-Gene Deficiency in vivo using a Single 'self-cleaving' 2A Peptide-Based Retroviral Vector," *Nature Biotech.*, vol. 22:589-594, 2004.
Tan et al., "Coexpression of double or triple copies of the rabies virus glycoprotein gene using a 'self-cleaving' 2A peptide-based replication-defective human adenovirus serotype 5 vector," *Biologicals* 38:586-593, 2010.
Finke et al., "Tracking Fluorescence-Labeled Rabies Virus: Enhanced Green Fluorescent Protein-Tagged Phosphoprotein P Supports Virus Gene Expression and Formation of Infectious Particles," *J Virol* 78(22): 12333-12343, 2004.

* cited by examiner

*Primary Examiner* — Rachel B Gill
(74) *Attorney, Agent, or Firm* — Klarquist Sparkman, LLP

(57) ABSTRACT

Recombinant adenovirus genomes that include an exogenous open reading frame (ORF) and a self-cleaving peptide coding sequence are described. Optimal placement of the exogenous genes for minimal impact on viral kinetics is further disclosed. Therapeutic applications of the recombinant adenoviruses are also described.

20 Claims, 13 Drawing Sheets
Specification includes a Sequence Listing.

FIG. 2
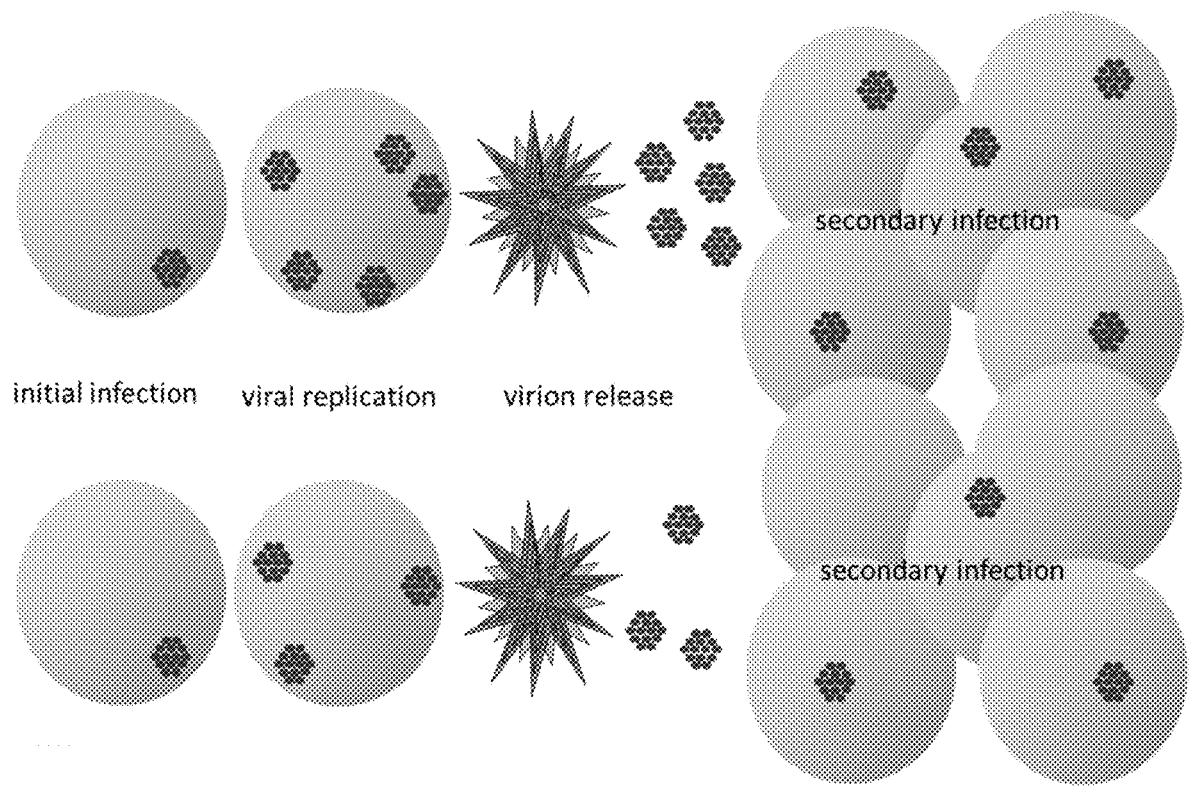
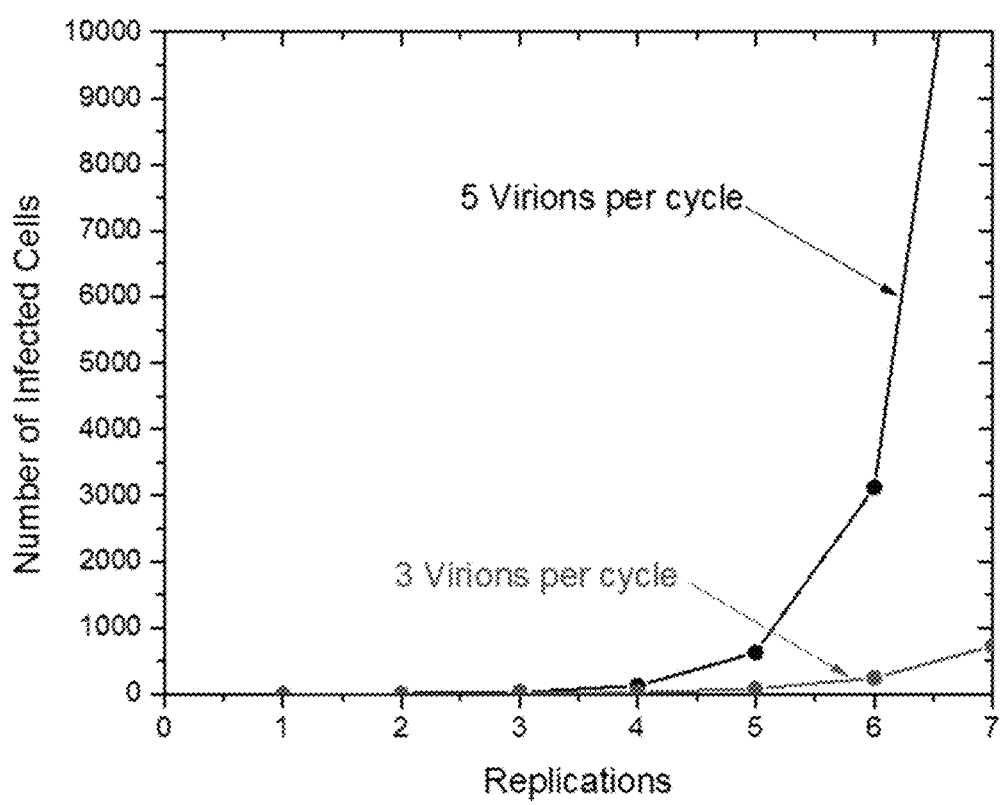

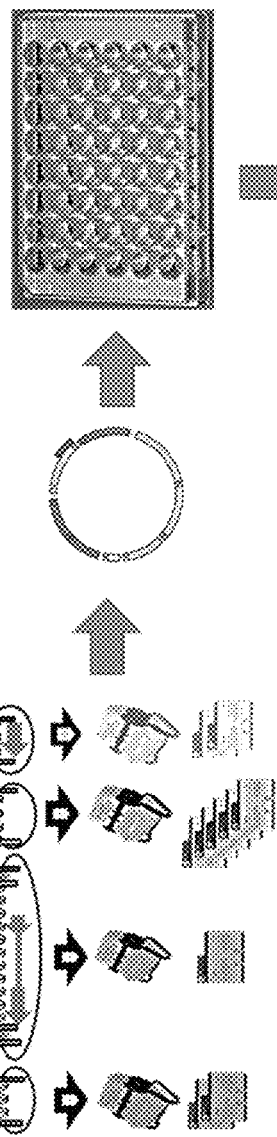
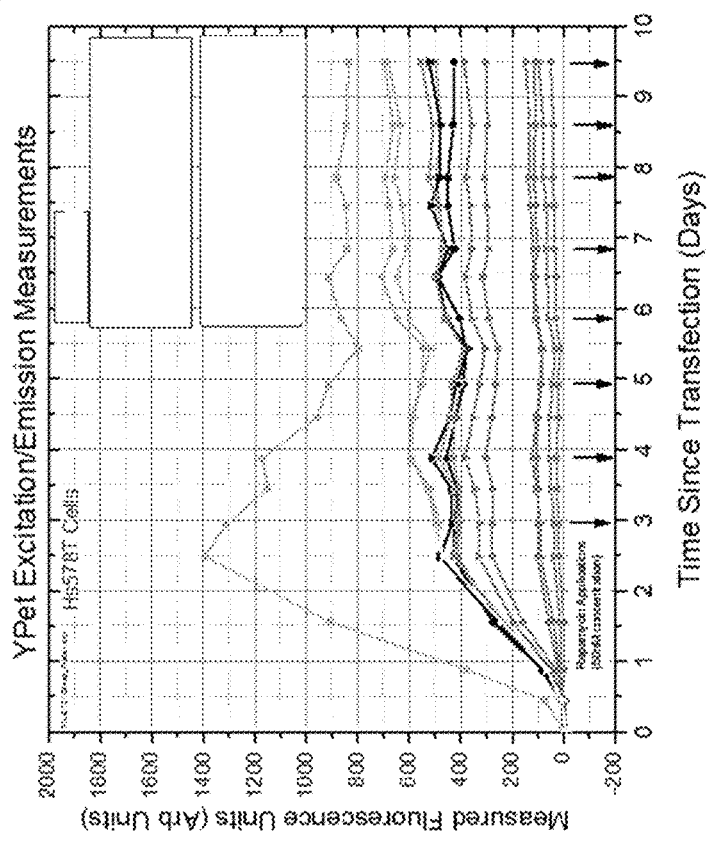
FIG. 3

FIG. 4A

Date: 140509
48 WELL PLATE NO: 2
Upper Half

Ratio of Xtreme Gene to DNA (ul : ug): 2
Dilution factor for Xtreme Gene to media: 0.03

| | 1 | 2 | 3 | 4 | 5 | 6 | 7 | 8 |
|---|---|---|---|---|---|---|---|---|
| | 500ng of CMBT-352 for 4 hours | 500ng of PCMN-389 for 4 hours | 500ng of CMBT-379 for 4 hours | 500ng of PCMN-422 for 4 hours | 500ng of CMBT-432 for 4 hours | 500ng of CMBT-403 for 4 hours | Mock | BLANK |
| Source DNA concentration (ng/ul): | 77.0 | 107.0 | 138.0 | 110.0 | 165.0 | 94.0 | 0.0 | N/A |
| Mass of DNA per tube A (ng): | 2000.0 | 2000.0 | 2000.0 | 2000.0 | 2000.0 | 2000.0 | 2000.0 | N/A |
| Volume of DMEM + 0% FBS per tube A (ul): | 133.3 | 133.3 | 133.3 | 133.3 | 133.3 | 133.3 | 133.3 | N/A |
| Volume of Xtreme Gene solution per tube A (ul): | 4.0 | 4.0 | 4.0 | 4.0 | 4.0 | 4.0 | 4.0 | N/A |
| Volume of DNA per tube A (ul): | 26.0 | 18.7 | 14.5 | 18.2 | 12.1 | 21.3 | 26.0 | N/A |
| Concentration of DNA in tube A (ng/ul): | 12.2 | 12.8 | 13.2 | 12.9 | 13.4 | 12.6 | 12.2 | N/A |
| Total volume in tube A (ul): | 163.3 | 156.0 | 151.8 | 155.5 | 149.5 | 158.6 | 163.3 | N/A |
| | | | | Vortex | | | | |
| | | | Incubate at room temperature for 15-30 minutes | | | | | |
| Volume of DMEM + 2% FBS per tube B (ul): | 557.1 | 563.5 | 567.2 | 563.9 | 569.2 | 561.2 | 557.1 | N/A |
| Volume of tube A added to tube B (ul): | 142.9 | 136.5 | 132.8 | 136.1 | 130.8 | 138.8 | 142.9 | N/A |
| Effective Percentage FBS: | 1.59 | 1.61 | 1.62 | 1.61 | 1.63 | 1.60 | 1.59 | N/A |
| Total volume in tube B (ul): | 700.0 | 700.0 | 700.0 | 700.0 | 700.0 | 700.0 | 700.0 | N/A |
| | | | | Vortex | | | | |
| Total DNA needed (ng): | 1750.0 | 1750.0 | 1750.0 | 1750.0 | 1750.0 | 1750.0 | 0.0 | N/A |
| Mass of DNA per well (ng): | 500.0 | 500.0 | 500.0 | 500.0 | 500.0 | 500.0 | 0.0 | N/A |
| Volume per well (ul): | 200.0 | 200.0 | 200.0 | 200.0 | 200.0 | 200.0 | 200.0 | N/A |

| | 1 | 2 | 3 | 4 | 5 | 6 | 7 | 8 |
|---|---|---|---|---|---|---|---|---|
| A | 1300 | 1300 | 1300 | 1300 | 1300 | 1300 | 1300 | 0 |
| B | 1300 | 1300 | 1300 | 1300 | 1300 | 1300 | 1300 | 0 |
| C | 1300 | 1300 | 1300 | 1300 | 1300 | 1300 | 1300 | 0 |

Total volume in wells (ul):
(Media after trans: DMEM + 10% FBS)

FIG. 4B

Date: 140509
48 WELL PLATE NO: 2
Lower Half

Ratio of Xtreme Gene to DNA (ul : ug): 2
Dilution factor for Xtreme Gene to media: 0.03

| | 1 | 2 | 3 | 4 | 5 | 6 | 7 | 8 |
|---|---|---|---|---|---|---|---|---|
| | 500ng of PCMN-421 for 4 hours | 500ng of CMBT-429 for 4 hours | 500ng of CMBT-428 for 4 hours | 500ng of CMBT-407 for 4 hours | 500ng of CMBT-426 for 4 hours | 500ng of CMBT-427 for 4 hours | 500ng of CMBT-424 for 4 hours | 500ng of CMBT-425 for 4 hours |
| Source DNA concentration (ng/ul): | 106.0 | 188.0 | 114.0 | 105.0 | 104.0 | 101.0 | 103.0 | 187.0 |
| Mass of DNA per tube A (ng): | 2000.0 | 2000.0 | 2000.0 | 2000.0 | 2000.0 | 2000.0 | 2000.0 | 2000.0 |
| Volume of DMEM + 0% FBS per tube A (ul): | 133.3 | 133.3 | 133.3 | 133.3 | 133.3 | 133.3 | 133.3 | 133.3 |
| Volume of Xtreme Gene solution per tube A (ul): | 4.0 | 4.0 | 4.0 | 4.0 | 4.0 | 4.0 | 4.0 | 4.0 |
| Volume of DNA per tube A (ul): | 18.9 | 10.6 | 17.5 | 19.0 | 19.2 | 19.8 | 19.4 | 10.7 |
| Concentration of DNA in tube A (ng/ul): | 12.8 | 13.5 | 12.9 | 12.8 | 12.8 | 12.7 | 12.8 | 13.5 |
| Total volume in tube A (ul): | 156.2 | 148.0 | 154.9 | 156.4 | 156.6 | 157.1 | 156.8 | 148.0 |

Vortex
Incubate at room temperature for 15-30 minutes

| Volume of DMEM + 2% FBS per tube B (ul): | 563.3 | 570.5 | 564.5 | 563.2 | 563.0 | 562.5 | 562.8 | 570.5 |
| Volume of tube A added to tube B (ul): | 136.7 | 129.5 | 135.5 | 136.8 | 137.0 | 137.5 | 137.2 | 129.5 |
| Effective Percentage FBS: | 1.61 | 1.63 | 1.61 | 1.61 | 1.61 | 1.61 | 1.61 | 1.63 |
| Total volume in tube B (ul): | 700.0 | 700.0 | 700.0 | 700.0 | 700.0 | 700.0 | 700.0 | 700.0 |

Vortex

| Total DNA needed (ng): | 1750.0 | 1750.0 | 1750.0 | 1750.0 | 1750.0 | 1750.0 | 1750.0 | 1750.0 |
| Mass of DNA per well (ng): | 500.0 | 500.0 | 500.0 | 500.0 | 500.0 | 500.0 | 500.0 | 500.0 |
| Volume per well (ul): | 200.0 | 200.0 | 200.0 | 200.0 | 200.0 | 200.0 | 200.0 | 200.0 |

| | 1 | 2 | 3 | 4 | 5 | 6 | 7 | 8 |
|---|---|---|---|---|---|---|---|---|
| D | 1300 | 1300 | 1300 | 1300 | 1300 | 1300 | 1300 | 1300 |
| E | 1300 | 1300 | 1300 | 1300 | 1300 | 1300 | 1300 | 1300 |
| F | 1300 | 1300 | 1300 | 1300 | 1300 | 1300 | 1300 | 1300 |

Total volume in wells (ul):
(Media after trans: DMEM + 10%FBS)

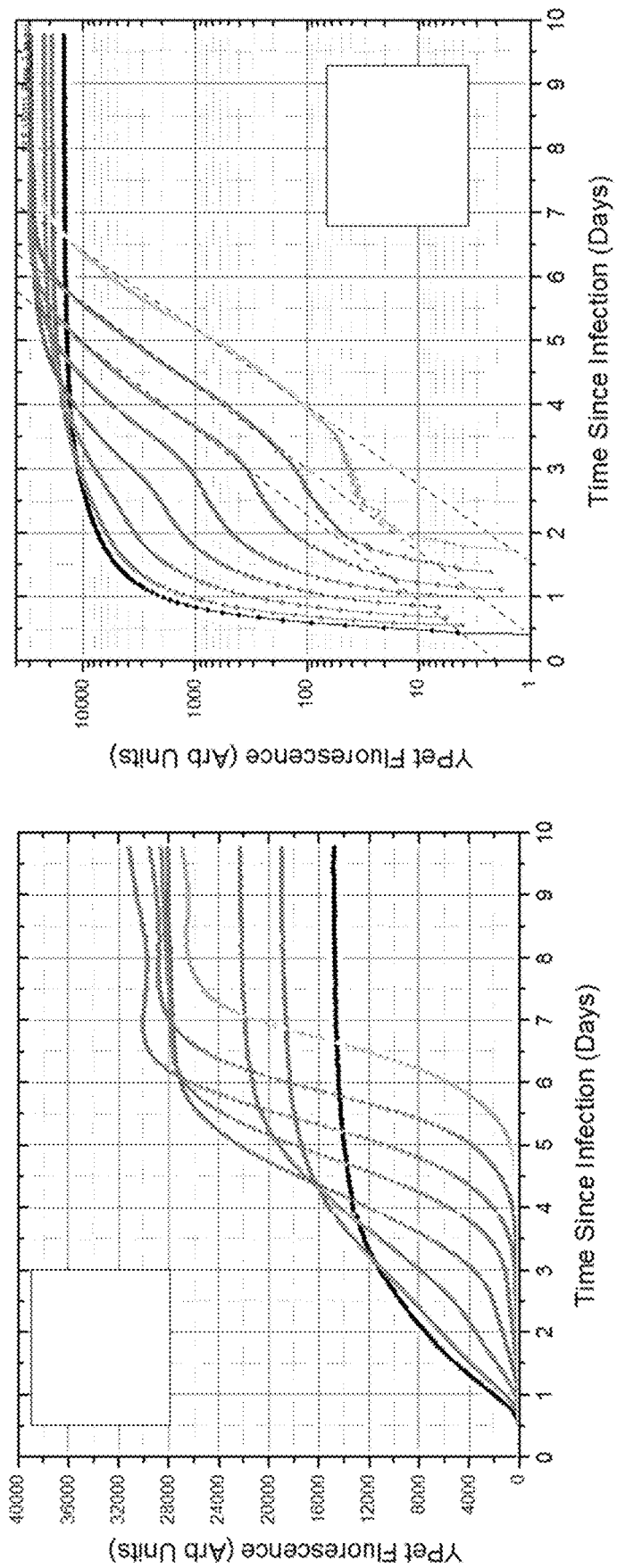
FIG. 8  Kinetics Data Analysis and Interpretation
- Fluorescence measured over multiple viral replication cycles
- Semi-log graph provides ln-slope
  - Similar analysis to yeast or bacteria growth curves
- Kinetics across viruses and cell lines can be compared
$$F(t) = Ae^{\alpha(t-t_0)} \implies \ln[F(t)] = \ln(A) + \alpha t - \alpha t_0$$

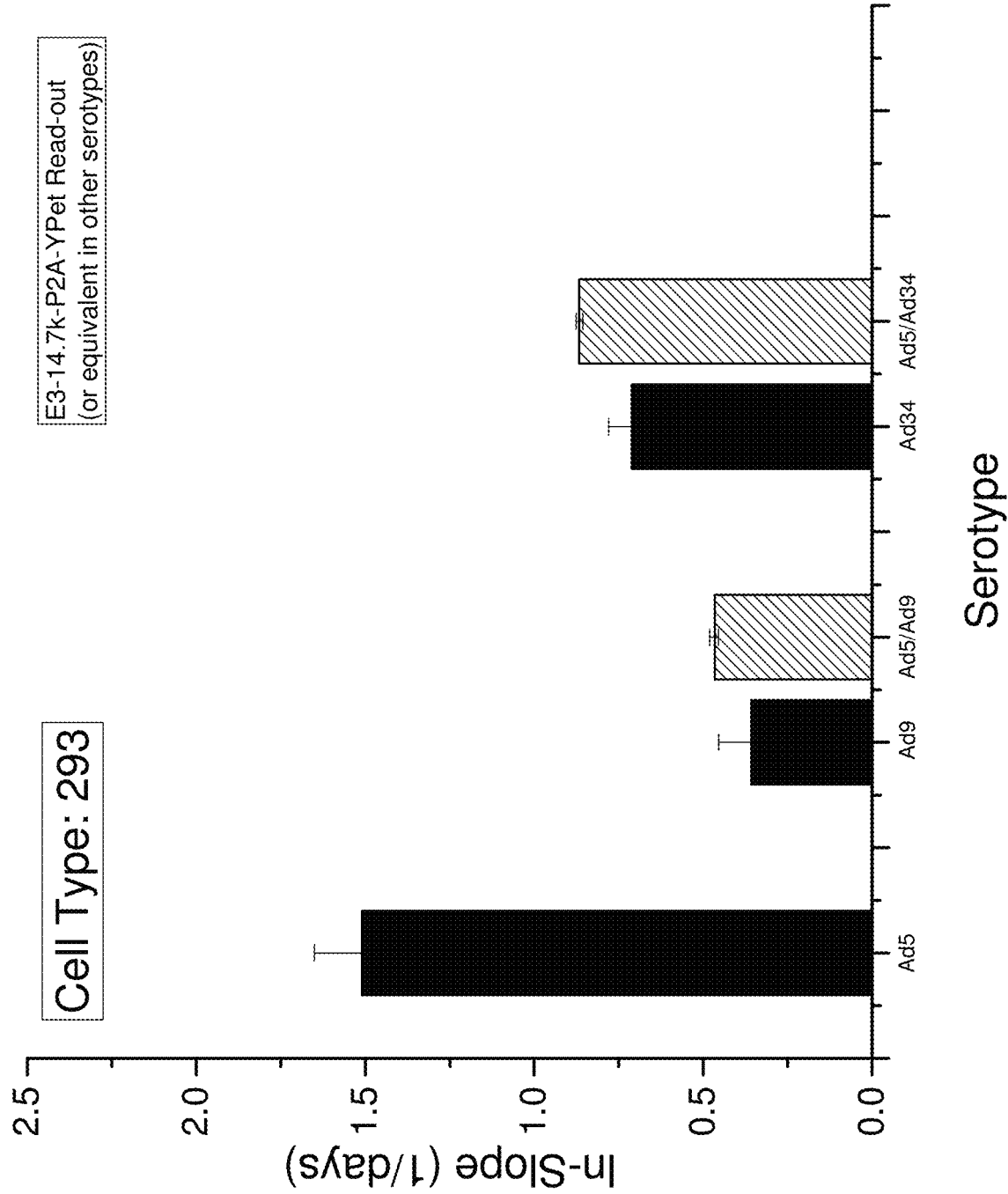

EXOGENOUS GENE EXPRESSION IN THERAPEUTIC ADENOVIRUS FOR MINIMAL IMPACT ON VIRAL KINETICS

CROSS REFERENCE TO RELATED APPLICATIONS

This application is a continuation of PCT International Application No. PCT/US2017/019086, filed Feb. 23, 2017, published in English under PCT Article 21(2), which claims the benefit of U.S. Provisional Application No. 62/298,653, filed Feb. 23, 2016. The above-referenced applications are herein incorporated by reference in their entirety.

FIELD

This disclosure concerns the optimal placement of exogenous open reading frames in recombinant adenovirus constructs and therapeutic applications of the recombinant viruses.

BACKGROUND

Adenovirus serotype 5 (Ad5) is the vector of choice in basic research applications, murine lung cancer models, and human gene therapy trials. Adenoviruses have a stable 36 kb double-stranded DNA genome protected by a protein capsid decorated with Ad fiber protein spikes that target infection to receptors on specific cell types. Adenoviruses do not integrate into host DNA, can be produced to high titers using established protocols, and have proven safety in human gene therapy and cancer applications. Thus, Ad-based vectors have enormous promise for cancer diagnostics and therapies.

SUMMARY

Disclosed herein are recombinant adenovirus genomes that include a heterologous open reading frame (ORF) and a self-cleaving peptide coding sequence. The heterologous ORF can encode, for example, a therapeutic protein. The recombinant adenovirus genomes and recombinant adenoviruses produced by the disclosed genomes can be used, for example, in therapeutic applications, such as for the treatment of cancer.

Provided herein are recombinant adenovirus genomes that include a heterologous ORF and a self-cleaving peptide coding sequence, both operably linked to and in the same reading frame as an endogenous adenovirus ORF. The self-cleaving peptide coding sequence is located between the heterologous ORF and the endogenous ORF. In some embodiments, the endogenous ORF is E1B-55k and the heterologous ORF is 3' of E1B-55k; the endogenous ORF is DNA polymerase and the heterologous ORF is 5' of DNA polymerase; the endogenous ORF is DNA-binding protein (DBP) and the heterologous ORF is 3' of DBP; the endogenous ORF is adenovirus death protein (ADP) and the heterologous ORF is 5' of ADP; the endogenous ORF is E3-14.7k and the heterologous ORF is 3' of E3-14.7k; the endogenous ORF is E4-ORF2 and the heterologous ORF is 5' of E4-ORF2; or the endogenous ORF is fiber and the heterologous ORF is 3' of fiber. In some examples, the heterologous ORF encodes a therapeutic protein.

Further provided herein are recombinant adenoviruses that include a recombinant adenovirus genome disclosed herein. Also provided are compositions that include a recombinant adenovirus genome or recombinant adenovirus disclosed herein and a pharmaceutically acceptable carrier.

Also provided is a method of delivering a therapeutic protein to a subject by administering to the subject a recombinant adenovirus genome or a recombinant adenovirus (or composition thereof) disclosed herein. In these methods, the heterologous ORF of the recombinant adenovirus genome or recombinant adenovirus encodes the therapeutic protein.

Further provided are methods of inhibiting tumor cell viability, inhibiting tumor cell growth, inhibiting tumor progression, reducing tumor volume and treating a subject with cancer by administering a recombinant adenovirus genome or a recombinant adenovirus (or composition thereof) disclosed herein. In these methods, the heterologous ORF of the recombinant adenovirus genome or recombinant adenovirus encodes a therapeutic protein suitable for the treatment of cancer.

The foregoing and other objects and features of the disclosure will become more apparent from the following detailed description, which proceeds with reference to the accompanying figures.

BRIEF DESCRIPTION OF THE DRAWINGS

FIG. 2 is a schematic showing exponential viral growth. Oncolytic killing of all cells within a tumor requires exponential viral growth. However, in most instances, only a small percentage of tumor cells are initially infected. Thus, a small difference in the number of progeny per round of replication leads to large differences in the total number of particles after just a few rounds of replication. Shown is a comparison between a virus that produces 3 virions per cycle and a virus that produces 5 virions per cycle. As shown in the graph, after 5-6 rounds of replication, viral titers of the two viruses are significantly different.

FIG. 3 is a schematic showing an exemplary work-flow of a fluorescence-based viral kinetic (FBVK) assay. Whole virus genome plasmid is produced (such as by Adsembly or AdSLIC) and used to transfect a cell type of interest in a multi-well plate. Alternatively, cells are infected with recombinant adenovirus particles. The adenovirus genome comprises at least one open reading frame (ORF) encoding a fluorescent protein in a location within the viral genome that does not substantially alter viral replication kinetics. Fluorescence is monitored over time to calculate viral replication kinetics. Oncolytic virus candidates are those exhibiting the largest differential in virus kinetics between tumor cells and normal cells.

FIGS. 4A-4B outline the kinetic assay setup when starting with adenovirus genome plasmids. This assay does not require accurate knowledge of initial transfection efficiency. Transfection conditions are selected to result in approximately 5-10% of cells initially transfected. In the example shown, a 48-well plate is used, which allows for the testing of 14 different virus constructs in triplicate, along with three mock-infected wells and three wells with FLUORESBRITE™ beads to compensate for tool sensitivity drift. (FIG. 4A) The wells of the upper half of the 48-well plate contain cells transfected with the genome plasmids of 6 different viruses, mock-infected cells, and blanks (FLUORESBRITE™ beads), each in triplicate. (FIG. 4B) The wells of the lower half of the 48-well plate contain cells transfected with the genome plasmids of 8 different viruses in triplicate. The multi-well plate is placed on a plate reader (such as a TECAN plate reader) for continuous fluorescence monitoring.

(FIG. 6A) The adenovirus genome is separated into four modules—E1, core, E3 and E4. (FIG. 6B) Adsembly involves genome reassembly using multi-site Gateway reactions. (FIG. 6C) AdSLIC utilizes sequence and ligation independent cloning (SLIC) to assemble adenovirus modules.

FIG. 8 is a schematic of kinetic data analysis and interpretation for the fluorescence-based viral kinetic assay.

FIGS. 9A-9C are bar graphs showing ln-slope values for recombinant adenoviruses derived from Ad5, Ad9 or Ad34 and containing a heterologous ORF 3' of the E3-14.7k ORF (or equivalent thereof in Ad9 and Ad34). Shown are the values for Ad5 (E3-14.7k-P2A-YPet; PCMN-887), Ad9 (E3-15k-P2A-YPet; PCMN-888) and Ad34 (E3-14.8k-P2A-YPet; PCMN-889) in 293 cells (FIG. 9A), A549 cells (FIG. 9B) and U2OS cells (FIG. 9C). Also shown in each figure are values for chimeric viruses comprising an Ad5 core (including E3-14.7k-P2A-YPet) and fiber shaft/knob from either Ad9 (Ad5/Ad9) or Ad34 (Ad5/Ad34).

SEQUENCE LISTING

Figure 1:
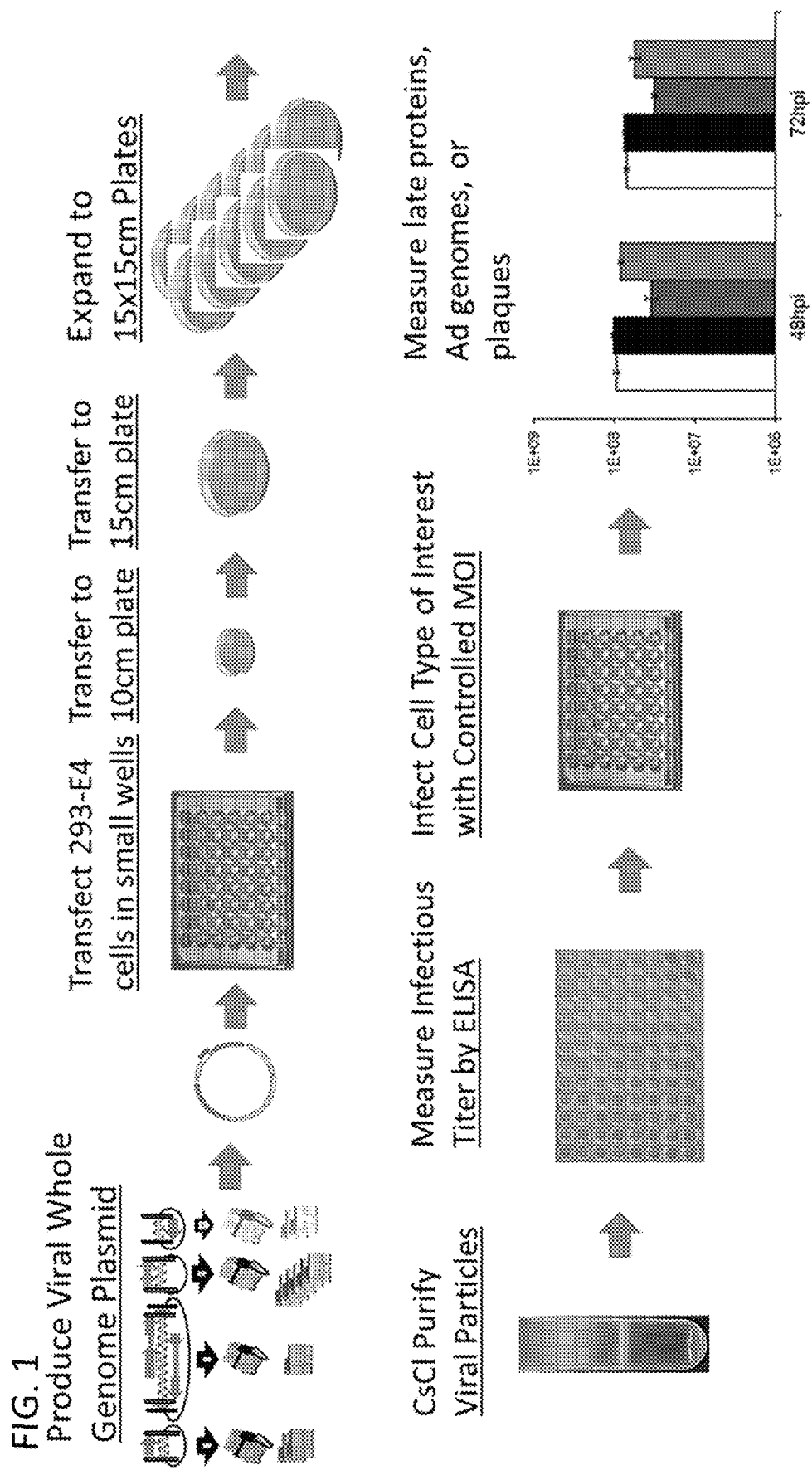
FIG. 1 is a schematic of an exemplary work-flow for testing adenoviral constructs. Whole virus genome plasmid is produced and transfected into suitable cells, such as 293-E4 cells, in a multi-well plate. As transfected cells expand, they are subjected to freeze/thaw to release viral particles, followed by centrifugation to pellet cell debris. The supernatant (containing the viral particles) is transferred to multiple, larger culture plates. Viral particles are harvested from transfected cells, CsCl purified and infectious virus titer is measured by ELISA. The cell type of interest is then infected with a known MOI of purified virus. At 48 or 72 hours post-infection, adenovirus late proteins, adenovirus genomes or plaques are measured by Western blot, q-PCR or plaque assay, respectively.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jul. 18, 2018, 703 KB, which is incorporated by reference herein. In the accompanying sequence listing:

SEQ ID NO: 1 is the nucleotide sequence of synthetic adenovirus genome CMBT-379 (YPet-P2A-E1A).

SEQ ID NO: 2 is the nucleotide sequence of synthetic adenovirus genome CMBT-432 (E1A-P2A-YPet).

SEQ ID NO: 3 is the nucleotide sequence of synthetic adenovirus genome CMBT-456 (E1B-55k-P2A-YPet).

SEQ ID NO: 4 is the nucleotide sequence of synthetic adenovirus genome CMBT-499 (E1B-55k-P2A-mCherry).

SEQ ID NO: 5 is the nucleotide sequence of synthetic adenovirus genome CMBT-530 (YPet-P2A-(DNA Poly)).

SEQ ID NO: 6 is the nucleotide sequence of synthetic adenovirus genome CMBT-886 (DBP-P2A-YPet).

SEQ ID NO: 7 is the nucleotide sequence of synthetic adenovirus genome CMBT-403 (YPet-P2A-ADP).

SEQ ID NO: 8 is the nucleotide sequence of synthetic adenovirus genome CMBT-429 (ADP-P2A-YPet).

SEQ ID NO: 9 is the nucleotide sequence of synthetic adenovirus genome PCMN-887 (E3-14.7k-P2A-YPet).

SEQ ID NO: 10 is the nucleotide sequence of synthetic adenovirus genome CMBT-457 (YPet-P2A-E4-ORF2).

SEQ ID NO: 11 is the nucleotide sequence of synthetic adenovirus genome CMBT-633 (mCherry-P2A-E4-ORF2).

SEQ ID NO: 12 is the nucleotide sequence of synthetic adenovirus genome CMBT-407 (YPet-P2A-Fiber).

SEQ ID NO: 13 is the nucleotide sequence of synthetic adenovirus genome CMBT-445 (Fiber-P2A-YPet).

SEQ ID NO: 14 is the amino acid sequence of P2A.

SEQ ID NO: 15 is the amino acid sequence of F2A.

SEQ ID NO: 16 is the amino acid sequence of E2A.

SEQ ID NO: 17 is the amino acid sequence of T2A.

SEQ ID NO: 18 is the amino acid sequence of a modified P2A comprising GSG at the N-terminus.

SEQ ID NO: 19 is the amino acid sequence of a modified F2A comprising GSG at the N-terminus.

SEQ ID NO: 20 is the amino acid sequence of a modified E2A comprising GSG at the N-terminus.

SEQ ID NO: 21 is the amino acid sequence of a modified T2A comprising GSG at the N-terminus.

SEQ ID NO: 22 is the nucleotide sequence of synthetic adenovirus genome PCMN-888 (Ad9 E3-15k-P2A-YPet).

SEQ ID NO: 23 is the nucleotide sequence of synthetic adenovirus genome PCMN-889 (Ad34 E3-14.8k-P2A-YPet).

DETAILED DESCRIPTION

I. Abbreviations

Ad adenovirus
ADP adenovirus death protein
BFP blue fluorescent protein
E2A equine rhinitis A virus 2A
ELISA enzyme-linked immunosorbent assay
ERAV equine rhinitis A virus
F2A foot and mouth disease virus 2A
FACS fluorescence activated cells sorting
FMDV food and mouth disease virus
GFP green fluorescent protein
MOI multiplicity of infection
OD optical density
ORF open reading frame
P2A porcine teschovirus-1 2A
pIX protein IX
PTV1 porcine teschovirus-1
RFP red fluorescent protein
SLIC sequence and ligation independent cloning
T2A Thosea asigna virus 2A TaV Thosea asigna virus
YFP yellow fluorescent protein

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

2A peptide: A type of self-cleaving peptide encoded by some RNA viruses, such as picornaviruses. 2A peptides function by making the ribosome skip the synthesis of a peptide bond at the C-terminus of a 2A element, leading to separation between the end of the 2A sequence and the downstream peptide (Kim et al., *PLoS One* 6(4):e18556, 2011). The "cleavage" occurs between the glycine and proline residues found on the C-terminus of the 2A peptide. Exemplary 2A peptides include, but are not limited to, the 2A peptides encoded by Thosea asigna virus (TaV), equine rhinitis A virus (ERAV), porcine teschovirus-1 (PTV1) and foot and mouth disease virus (FMDV), which are set forth herein as SEQ ID NOs: 14-17). In some embodiments, the 2A peptide comprises Gly-Ser-Gly at the N-terminus to improve cleavage efficiency (SEQ ID NOs: 18-21).

Adenovirus: A non-enveloped virus with a linear, double-stranded DNA genome and an icosahedral capsid. There are currently 68 known serotypes of human adenovirus, which are divided into seven species (species A, B, C, D, E, F and G). Different serotypes of adenovirus are associated with different types of disease, with some serotypes causing respiratory disease (primarily species B and C), conjunctivitis (species B and D) and/or gastroenteritis (species F and G).

Adenovirus death protein (ADP): A protein synthesized in the late stages of adenovirus infection that mediates lysis of cells and release of adenovirus to infect other cells. ADP is an integral membrane glycoprotein of 101 amino acids that localizes to the nuclear membrane, endoplasmic reticulum and Golgi. ADP was previously named E3-11.6K).

Administration: To provide or give a subject an agent, such as a therapeutic agent (e.g. a recombinant virus), by any effective route. Exemplary routes of administration include, but are not limited to, injection (such as subcutaneous, intramuscular, intradermal, intraperitoneal, intratumoral, and intravenous), oral, intraductal, sublingual, rectal, transdermal, intranasal, vaginal and inhalation routes.

Chimeric: Composed of at least two parts having different origins. In the context of the present disclosure, a "chimeric adenovirus" is an adenovirus having genetic material and/or proteins derived from at least two different serotypes (such as from Ad5 and a second serotype of adenovirus). In this context, a "capsid-swapped" adenovirus refers to a chimeric adenovirus in which the capsid proteins are derived from one serotype of adenovirus and the remaining proteins are derived from another adenovirus serotype. Similarly, a "chimeric fiber" is a fiber protein having amino acid sequence derived from at least two different serotypes of adenovirus. For example, a chimeric fiber can be composed of a fiber shaft from Ad5 and a fiber knob from a second serotype of adenovirus. In another example, a chimeric fiber is composed of an Ad5 tail and a fiber shaft and knob from a second serotype of adenovirus (such as Ad9 or Ad34).

Contacting: Placement in direct physical association; includes both in solid and liquid form.

Degenerate variant: In the context of the present disclosure, a "degenerate variant" refers to a polynucleotide encoding a peptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Deleted: An adenovirus genome encoding a "deleted" protein (such as the E4orf1 or E4orf6/7 protein) refers to an adenovirus having a complete deletion of the protein coding sequence, or a partial deletion that results in the absence of protein expression.

Deregulation of E2F: Refers to an increase in activity of the E2F transcription factor and downstream target genes, which occurs in nearly all types of human cancer. Deregulation of the E2F pathway activity and transcription can result from a variety of different mutations in any upstream component of the pathway, such as loss of function mutations and deletions in Rb, p107 and p130 tumor suppressors. Rb was the first tumor suppressor to be identified and is absent or mutated in at least one third of human tumors. In addition, p16 mutations and/or epigenetic silencing can activate E2F in tumor cells. Cyclin D and CDK4 mutations, gene amplifications or over-expression can also result in deregulated E2F activity in human tumors. In addition E2F is activated by growth factor receptor pathway mutations including EGFR, RTKs, RAS, RAF, PI-3K, PTEN, RAF, MYC. Mutations in the $p16^{INK4a}$-Cyclin D:cdk4/6-RB-E2F pathway generally occur in a mutually exclusive fashion, so that one 'hit' (for example, p16) is unaccompanied by others (for example, Rb mutation or cyclin D:cdk over-expression). However, most current chemotherapies are proliferative poisons that inhibit E2F transcriptional targets, but are also toxic to normal cells and have often devastating iatrogenic complications. As disclosed herein, an alternative therapeutic approach is to use a virus that undergoes selective lytic replication in cancer cell lesions that have deregulated the p16-cyclin D:cdk4-RB-E2F pathway.

DNA-binding protein (DBP): This adenovirus protein binds to single-stranded DNA and RNA, as well as double-stranded DNA. DBP, a 72-kilodalton protein, is essential for replication of adenoviral DNA.

E1A: The adenovirus early region 1A (E1A) gene and polypeptides expressed from the gene. The E1A protein plays a role in viral genome replication by driving cells into the cell cycle. As used herein, the term "E1A protein" refers to the proteins expressed from the E1A gene and the term includes E1A proteins produced by any adenovirus serotype.

E3-RIDα/RIDβ and E3-14.7k: Early-expressed proteins produced from the E3 gene. The E3-RIDα, E3-RIDβ, and E3-14.7k proteins make up the receptor internalization and degradation complex (RID), which localizes to the nuclear membrane and causes the endocytosis and degradation of a variety of receptors including CD95 (FasL receptor), and TNFR1 and 2 (TNF/TRAIL receptors) to protect infected cells from host antiviral responses. The E3-RIDα, E3-RIDβ, and E3-14.7k coding sequences are next to each other, in this order.

E4orf1: An adenovirus protein produced from the E4 gene. The term "E4orf1 protein" includes E4orf1 proteins produced by the E4 gene from any adenovirus serotype.

E4orf6/7: A protein encoded by the adenovirus E4 gene. The term "E4orf6/7 protein" includes E4orf6/7 proteins produced by the E4 gene from any adenovirus serotype.

Fiber: The adenovirus fiber protein is a trimeric protein that mediates binding to cell surface receptors. The fiber protein is comprised of a long N-terminal shaft and globular C-terminal knob.

Fluorescent protein: A protein that emits light of a certain wavelength when exposed to a particular wavelength of light. Fluorescent proteins include, but are not limited to, green fluorescent proteins (such as GFP, EGFP, AcGFP1, Emerald, Superfolder GFP, Azami Green, mWasabi, TagGFP, TurboGFP and ZsGreen), blue fluorescent proteins (such as EBFP, EBFP2, Sapphire, T-Sapphire, Azurite and mTagBFP), cyan fluorescent proteins (such as ECFP, mECFP, Cerulean, CyPet, AmCyanl, Midori-Ishi Cyan, mTurquoise and mTFP1), yellow fluorescent proteins (EYFP, Topaz, Venus, mCitrine, YPet, TagYFP, PhiYFP, ZsYellowl and mBanana), orange fluorescent proteins (Kusabira Orange, Kusabira Orange2, mOrange, mOrange2 and mTangerine), red fluorescent proteins (mRuby, mApple, mStrawberry, AsRed2, mRFP1, JRed, mCherry, HcRed1, mRaspberry, dKeima-Tandem, HcRed-Tandem, mPlum, AQ143, tdTomato and E2-Crimson), orange/red fluorescence proteins (dTomato, dTomato-Tandem, TagRFP, TagRFP-T, DsRed, DsRed2, DsRed-Express (T1) and DsRed-Monomer) and modified versions thereof.

Fusion protein: A protein containing amino acid sequence from at least two different (heterologous) proteins or peptides. Fusion proteins can be generated, for example, by expression of a nucleic acid sequence engineered from nucleic acid sequences encoding at least a portion of two different (heterologous) proteins. To create a fusion protein, the nucleic acid sequences must be in the same reading frame and contain no internal stop codons. Fusion proteins, particularly short fusion proteins, can also be generated by chemical synthesis.

Heterologous: A heterologous protein or polypeptide refers to a protein or polypeptide derived from a different source or species.

Hexon: A major adenovirus capsid protein.

Immunomodulator: An agent that alters (e.g. activates, enhances or suppresses) the immune system. Immunomodulators include, but are not limited to, cytokines (such as interleukin 2 (IL-2), IL-7, IL-12, GM-CSF, FLT3 ligand, or interferons), chemokines (such as CCL3, CCL26, CXCL7, CXCL9, and CXCL10), T cell activating ligands (such as anti-CD3 Abs or alloantigens), co-stimulatory molecules (such as B7.1/B7.2, OX40L, 4-1-BBL or CD40L), checkpoint blockade inhibitors (such as anti-PD-1 or anti-CTLA4 Abs), and small molecule immunomodulators.

Isolated: An "isolated" biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Modification: A change in the sequence of a nucleic acid or protein sequence. For example, amino acid sequence modifications include, for example, substitutions, insertions and deletions, or combinations thereof. Insertions include amino and/or carboxyl terminal fusions as well as intrasequence insertions of single or multiple amino acid residues. Deletions are characterized by the removal of one or more amino acid residues from the protein sequence. In some embodiments herein, the modification (such as a substitution, insertion or deletion) results in a change in function, such as a reduction or enhancement of a particular activity of a protein. As used herein, "Δ" or "delta" refer to a deletion. Substitutional modifications are those in which at least one residue has been removed and a different residue inserted in its place. Amino acid substitutions are typically of single residues, but can occur at a number of different locations at once. Substitutions, deletions, insertions or any combination thereof may be combined to arrive at a final mutant sequence. These modifications can be prepared by modification of nucleotides in the DNA encoding the protein, thereby producing DNA encoding the modification. Techniques for making insertion, deletion and substitution mutations at predetermined sites in DNA having a known sequence are well known in the art. A "modified" protein, nucleic acid or virus is one that has one or more modifications as outlined above.

Neoplasia, malignancy, cancer and tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Malignant tumors are also referred to as "cancer."

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. In some cases, lymphomas are considered solid tumors.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, human papilloma virus (HPV)-infected neoplasias, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastasis).

Oncolytic virus: A virus that selectively kills cells of a proliferative disorder, e.g., cancer/tumor cells. Killing of the cancer cells can be detected by any method established in the art, such as determining viable cell count, or detecting cytopathic effect, apoptosis, or synthesis of viral proteins in the cancer cells (e.g., by metabolic labeling, immunoblot, or RT-PCR of viral genes necessary for replication), or reduction in size of a tumor.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents (e.g. a recombinant virus disclosed herein).

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide, peptide or protein: A polymer in which the monomers are amino acid residues which are joined together through amide bonds. When the amino acids are alpha-amino acids, either the L-optical isomer or the D-optical isomer can be used. The terms "polypeptide," "peptide" and "protein" are used interchangeably herein. These terms apply to amino acid polymers in which one or more amino acid residue is an artificial chemical mimetic of a corresponding naturally occurring amino acid, as well as to naturally occurring amino acid polymers and non-naturally occurring amino acid polymers. The term "residue" or "amino acid residue" includes reference to an amino acid that is incorporated into a protein, polypeptide, or peptide.

A conservative substitution in a polypeptide is a substitution of one amino acid residue in a protein sequence for a different amino acid residue having similar biochemical properties. Typically, conservative substitutions have little to no impact on the activity of a resulting polypeptide. For example, a protein or peptide including one or more conservative substitutions (for example no more than 1, 2, 3, 4 or 5 substitutions) retains the structure and function of the wild-type protein or peptide. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A region of DNA that directs/initiates transcription of a nucleic acid (e.g. a gene). A promoter includes necessary nucleic acid sequences near the start site of transcription. Typically, promoters are located near the genes they transcribe. A promoter also optionally includes distal enhancer or repressor elements which can be located as much as several thousand base pairs from the start site of transcription. A "constitutive promoter" is a promoter that is continuously active and is not subject to regulation by external signals or molecules. In contrast, the activity of an "inducible promoter" is regulated by an external signal or molecule (for example, a transcription factor or tetracycline).

Protein IX (pIX): A minor component of the adenovirus capsid that associates with the hexon protein.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule, protein or virus is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques. The term "recombinant" also includes nucleic acids, proteins and viruses that have been altered solely by addition, substitution, or deletion of a portion of the natural nucleic acid molecule, protein or virus.

Replication defects: An adenovirus that exhibits "replication defects" in a non-tumor cell (compared to a tumor cell) refers to an adenovirus that exhibits reduced viral replication in normal cells compared to tumor cells. Replication defects are evidenced by, for example, a lack of viral late protein expression, a reduction in viral DNA synthesis, a reduced ability to induce E2F target genes (e.g. cyclin A and B), a reduced ability to elicit S phase entry and/or a reduced ability to induce cell killing in normal cells compared to tumor cells.

Replication deficient virus: A virus that preferentially inhibits cell proliferation, causes cell lysis, or induces apoptosis (collectively considered killing) in a predetermined cell population with a given phenotype (e.g., tumor cells with a deregulated E2F pathway). Such viruses are unable to or are limited in the ability to reduce or inhibit cell proliferation, cause cell lysis, induce apoptosis, or otherwise replicate in cells that do not have the predetermined cell phenotype (such as normal, non-tumor cells).

Self-cleaving peptides: Peptides that induce the ribosome to skip the synthesis of a peptide bond at the C-terminus, leading to separation of the peptide sequence and a downstream polypeptide. Virally encoded 2A peptides are a type of self-cleaving peptide. Virally encoded 2A peptides include, for example, 2A peptides from porcine teschovirus-1 (PTV1), foot and mouth disease virus (FMDV), equine rhinitis A virus (ERAV) and Thosea asigna virus (TaV).

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Serotype: A group of closely related microorganisms (such as viruses) distinguished by a characteristic set of antigens.

Subject: Living multi-cellular vertebrate organisms, a category that includes human and non-human mammals.

Synthetic: Produced by artificial means in a laboratory, for example a synthetic nucleic acid or protein can be chemically synthesized in a laboratory.

Therapeutic agent: Any agent capable of inducing a desired therapeutic or prophylactic effect when properly administered to a subject. Therapeutic agents include, but are not limited to, chemical compounds, small molecules, recombinant viruses, antisense compounds, antibodies (or antigen-binding fragments thereof), peptides or nucleic acid molecules. For example, therapeutic agents for treating cancer include agents that prevent or inhibit tumor growth, tumor development, or tumor metastasis. "Therapeutic proteins" are therapeutic agents that are proteins or peptides, including antibodies or antigen-binding fragments thereof. In some embodiments herein, the therapeutic protein is an immunomodulator. In other embodiments, the therapeutic protein comprises a toxin, Fas or FasL, a soluble death factor, a mediator of bystander destruction, a tumor antigen, a neo antigen or an alloantigen.

Therapeutically effective amount: A quantity of a specified pharmaceutical or therapeutic agent (e.g. a recombinant virus) sufficient to achieve a desired effect in a subject, or in a cell, being treated with the agent. The effective amount of the agent can be dependent on several factors, including, but not limited to the subject or cells being treated, and the manner of administration of the therapeutic composition.

Uexon: An open reading frame located on the/strand (leftward transcription) between the early E3 region and the fiber gene (Tollefson et al., *J Virol* 81(23):12918-12926).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Embodiments

Disclosed herein are recombinant adenovirus genomes that include a heterologous open reading frame (ORF) and a self-cleaving peptide coding sequence. The heterologous ORF can encode, for example, a therapeutic protein (such as an immunomodulator). The recombinant adenovirus genomes and recombinant adenoviruses produced by the disclosed genomes can be used, for example, in a variety of different therapeutic applications, such as the treatment of cancer.

Provided herein are recombinant adenovirus genomes that include a heterologous ORF and a self-cleaving peptide coding sequence, both operably linked to and in the same reading frame as an endogenous adenovirus ORF. The self-cleaving peptide coding sequence is located between the heterologous ORF and the endogenous ORF. In some embodiments, the endogenous ORF is E1B-55k and the heterologous ORF is 3' of E1B-55k; the endogenous ORF is DNA polymerase and the heterologous ORF is 5' of DNA polymerase; the endogenous ORF is DNA-binding protein (DBP) and the heterologous ORF is 3' of DBP; the endogenous ORF is adenovirus death protein (ADP) and the heterologous ORF is 5' of ADP; the endogenous ORF is E3-14.7k and the heterologous ORF is 3' of E3-14.7k; the endogenous ORF is E4-ORF2 and the heterologous ORF is 5' of E4-ORF2; or the endogenous ORF is fiber and the heterologous ORF is 3' of fiber.

In some embodiments, the heterologous ORF encodes a therapeutic protein.

In some embodiments, the self-cleaving peptide is a 2A peptide or variant thereof. In some examples, the 2A peptide includes a porcine teschovirus-1 (PTV1) 2A (P2A) peptide, a foot and mouth disease virus (FMDV) 2A (F2A) peptide, an equine rhinitis A virus (ERAV) 2A (E2A) peptide or a Thosea asigna virus (TaV) 2A (T2A) peptide, or a variant thereof. In particular examples, the P2A peptide sequence is at least 80%, at least 85%, at least 90%, at least 95%, at least 96%, at least 97%, at least 98% or at least 99% identical to the amino acid sequence of SEQ ID NO: 14 or SEQ ID NO: 18. In some examples, the 2A peptide variant comprises additional amino acid sequence (such as GSG) at the N-terminus.

In particular examples, the F2A peptide sequence is at least 80%, at least 85%, at least 90%, at least 95%, at least 96%, at least 97%, at least 98% or at least 99% identical to the amino acid sequence of SEQ ID NO: 15 or SEQ ID NO: 19. In particular examples, the E2A peptide sequence is at least 80%, at least 85%, at least 90%, at least 95%, at least 96%, at least 97%, at least 98% or at least 99% identical to the amino acid sequence of SEQ ID NO: 16 or SEQ ID NO: 20. In particular examples, the T2A peptide sequence is at least 80%, at least 85%, at least 90%, at least 95%, at least 96%, at least 97%, at least 98% or at least 99% identical to the amino acid sequence of SEQ ID NO: 17 or SEQ ID NO: 21. In specific non-limiting examples, the self-cleaving peptide comprises or consists of the amino acid sequence of any one of SEQ ID NOs: 14-21.

In some embodiments, the adenovirus is an adenovirus type 5 (Ad5). In other embodiments, the adenovirus is an Ad2, Ad3, Ad9, Ad11, Ad12 or Ad34. In yet other embodiments, the adenovirus is a chimeric adenovirus, such as, but not limited to, an Ad5/Ad9 or Ad5/Ad34 chimeric adenovirus.

Further provided herein are recombinant adenoviruses that include a recombinant adenovirus genome disclosed herein.

The recombinant adenoviruses (and recombinant adenovirus genomes) provided herein optionally include additional modifications, such as to target the virus to specific cell types, to inhibit targeting to and replication in the liver, to allow for selective replication in tumor cells, and to evade pre-existing neutralizing antibodies to common adenovirus serotypes. The additional modifications can vary depending on the desired use of the recombinant adenovirus. Adenovirus modifications are described, for example, in PCT Application No. PCT/US2015/051745 (filed Sep. 23, 2015), WO 2012/024350, WO 2013/138505 and WO 2014/153204, which are herein incorporated by reference in their entirety.

Compositions that include a recombinant adenovirus genome, or a recombinant adenovirus, and a pharmaceutically acceptable carrier are also provided by the present disclosure.

Also provided herein are methods of delivering a therapeutic protein to a subject. In some embodiments, the method includes administering to the subject a recombinant adenovirus genome, a recombinant adenovirus, or a composition disclosed herein. In these methods, the heterologous ORF of the recombinant adenovirus or recombinant adenovirus genome encodes the therapeutic protein.

Further provided are methods of reducing or inhibiting tumor cell viability and/or tumor cell growth (for example a reduction of at least 10%, at least 20%, at least 30%, at least 40%, at least 50%, at least 75%, at least 90%, at least 95%, or at least 98%, as compared to an absence of the disclosed therapy). In some embodiments, the method includes contacting the tumor cell with a recombinant adenovirus genome, a recombinant adenovirus, or a composition disclosed herein. In these methods, the heterologous ORF encodes a therapeutic protein. In some examples, the method is an in vitro method. In other examples, the method is an in vivo method and contacting the tumor cell includes administering the recombinant adenovirus genome, recombinant adenovirus, or composition to a subject with a tumor.

Methods of reducing or inhibiting tumor progression, such as by reducing the number and/or size of a metastasis, or reducing tumor volume in a subject are further provided herein (for example a reduction of at least 10%, at least 20%, at least 30%, at least 40%, at least 50%, at least 75%, at least 90%, at least 95%, or at least 98%, as compared to an absence of the disclosed therapy). In some embodiments, the method includes administering to the subject a therapeutically effective amount of a recombinant adenovirus genome, a recombinant adenovirus, or a composition disclosed herein. In these methods, the heterologous ORF encodes a therapeutic protein.

Further provided are methods of treating cancer in a subject. In some embodiments, the method includes administering to the subject a therapeutically effective amount of a recombinant adenovirus genome, a recombinant adenovirus, or a composition disclosed herein. In these methods, the heterologous ORF encodes a therapeutic protein.

In some embodiments herein, the method further includes administering an additional therapeutic agent to the subject. For example, the additional therapeutic agent may include an anti-cancer agent, such as a chemotherapeutic agent, a biologic (such as an antibody or fragment thereof, such as a monoclonal antibody), or a nucleic acid molecule, such as an inhibitory nucleic acid molecule) or other therapeutic treatment, such as surgical resection of a tumor or irradiation of a tumor.

Also provided herein are kits that include a recombinant adenovirus genome, a recombinant adenovirus, or a composition disclosed herein; and one or more additional therapeutic agents and/or one or more diagnostic agents. In some embodiments, the one or more additional therapeutic agents include a chemotherapeutic, biologic, or combinations thereof. In some examples, the one or more diagnostic agents include one or more antibodies or nucleic acid molecules specific for a tumor marker, or an imaging probe that can be used to track the virus or tumor cells in vitro or in vivo.

IV. Optimal Placement of Exogenous ORFs

The 36kb adenovirus genome is compact, using both the top and bottom strands for coding of various genes. At many locations within the adenovirus genome, both the top and bottom strand are used simultaneously for coding separate genes. The genome size has evolved to be optimal for insertion into its capsid. As a result, the insertion of exogenous genes is limited by the size capacity of the capsid as excessive addition of exogenous nucleic acid leads to incomplete genome loading into the capsid and reduced viral kinetics.

A solution to the challenge presented by the limited available space in the adenovirus genome is to locate exogenous open reading frames (ORFs) as fusion products within native adenovirus ORFs. This strategy makes use of adenovirus promoters, 5'UTRs, and polyA tails already encoded in the genome. However, expression of a fusion between a native adenovirus protein and an exogenous protein can be deleterious to one or both protein functions and lead to a significant decrease in adenovirus replication kinetics.

The present disclosure provides a solution to this problem by using a self-cleaving peptide sequence placed between the native (endogenous) ORF and the exogenous (heterologous) ORF. When placed between the two ORFs on a single mRNA, the presence of the self-cleaving peptide sequence leads to ribosome skipping and release of the first protein separate from the second protein. In some embodiments disclosed herein, the self-cleaving peptide is a 2A peptide (P2A).

Also disclosed herein is the identification of optimal placement sites for heterologous ORFs within the adenovirus genome. The combination of the self-cleaving peptide sequence and the judicious placement of the heterologous ORF leads to high expression and minimal to no impact on viral kinetics.

As described in Example 1 below, several sites within the adenovirus genome were identified that upon insertion of a heterologous ORF, did not inhibit adenovirus replication kinetics. In particular, it was determined that a heterologous ORF could be inserted C-terminal to the E1B-55k ORF, N-terminal to the DNA polymerase ORF, C-terminal to the DBP ORF, N-terminal to the ADP ORF, C-terminal to the E3-14.7k ORF or N-terminal to E4-ORF2. In each instance, a self-cleaving peptide sequence (P2A site) was inserted between the adenovirus ORF and the heterologous ORF. It is further disclosed herein that insertion of a heterologous ORF C-terminal to fiber produced a replication defective adenovirus; however, the recombinant virus was capable of producing extraordinarily high levels of heterologous protein in infected cells, which could prove useful in a number of therapeutic applications.

Therefore, the present disclosure contemplates the use of the following recombinant adenoviruses for therapeutic applications (where "SC" refers to a sequence encoding a self-cleaving peptide, such as P2A):

E1B-55k-SC-heterologous ORF heterologous ORF-SC-(DNA polymerase)

DBP-SC-heterologous ORF heterologous ORF-SC-ADP

E3-14.7k-SC-heterologous ORF heterologous ORF-SC-E4-ORF2 fiber-SC-heterologous ORF

In some embodiments herein, the self-cleaving peptide is a virally encoded 2A peptide, or a modified version thereof as described further below.

V. Self-Cleaving Peptide Sequences

Self-cleaving peptides are peptides that induce the ribosome to skip the synthesis of a peptide bond at the C-terminus, leading to separation of the peptide sequence and a downstream polypeptide. The use of self-cleaving peptides allows for expression of multiple proteins flanking the self-cleaving peptide from a single ORF. Virally encoded 2A peptides are one type of self-cleaving peptide.

As with other self-cleaving peptides, 2A peptides function by making the ribosome skip the synthesis of a peptide bond at the C-terminus of a 2A element, leading to separation between the end of the 2A sequence and the downstream peptide (Kim et al., *PLoS One* 6(4):e18556, 2011). The "cleavage" occurs between the glycine and proline residues found on the C-terminus of the 2A peptide. Exemplary 2A peptides include, but are not limited to, the 2A peptides encoded by Thosea asigna virus (TaV), equine rhinitis A virus (ERAV), porcine teschovirus-1 (PTV1) and foot and mouth disease virus (FMDV), or modified versions thereof In particular examples herein, the 2A peptide comprises PTV1 2A (P2A), FMDV 2A (F2A), ERAV 2A (E2A) or TaV 2A (T2A), the sequences of which are show below and are set forth herein as SEQ ID NOs: 14-17.

```
                                           (SEQ ID NO: 14)
         P2A: ATNFSLLKQAGDVEENPGP (SEQ ID NO: 15)
         F2A: VKQTLNFDLLKLAGDVESNPGP (SEQ ID NO: 16)
         E2A: QCTNYALLKLAGDVESNPGP (SEQ ID NO: 17)
         T2A: EGRGSLLTCGDVEENPGP
```

In some examples, the 2A peptide is modified to include Gly-Ser-Gly at the N-terminus to improve cleavage efficiency. The sequences of modified P2A, F2A, E2A and T2A are shown below and are set forth herein as SEQ ID NOs: 18-21.

Modified P2A: GSGATNFSLLKQAGDVEENPGP (SEQ ID NO: 18)

Modified F2A: GSGVKQTLNFDLLKLAGDVESNPGP (SEQ ID NO: 19)

Modified E2A: GSGQCTNYALLKLAGDVESNPGP (SEQ ID NO: 20)

Modified T2A: GSGEGRGSLLTCGDVEENPGP (SEQ ID NO: 21)

In some embodiments, the 2A polypeptide is a variant of a 2A polypeptide disclosed herein. Variants can include polypeptide sequences having at least 80%, at least 85%, at least 90%, at least 95%, at least 96%, at least 97%, at least 98%, at least 99%, or more, sequence identity to a wild-type or modified 2A polypeptide disclosed herein. Variants can include, for example, a deletion of at least one N-terminal amino acid from the 2A polypeptide of any one of SEQ ID NOs: 14-21, for example a deletion of 1, 2, 3, 4 or 5 amino acids, including ranges between any two of the listed values. Variants can include a deletion of at least one C-terminal amino acid from the 2A polypeptide of any one of SEQ ID NOs: 14-21, for example a deletion of 1, 2, 3, 4 or 5 amino acids, including ranges between any two of the listed values. Variants can also include, for example, at least 1, 2, 3, 4 or 5 amino acid substitutions, such as conservative amino acid substitutions.

VI. Pharmaceutical Compositions

Provided herein are compositions comprising a recombinant adenovirus or a recombinant adenovirus genome. The compositions are, optionally, suitable for formulation and administration in vitro or in vivo. Optionally, the compositions comprise one or more of the provided agents and a pharmaceutically acceptable carrier. Suitable carriers and their formulations are described in *Remington: The Science and Practice of Pharmacy*, 22nd Edition, Loyd V. Allen et al., editors, Pharmaceutical Press (2012). Pharmaceutically acceptable carriers include materials that are not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

The recombinant viruses (or one or more nucleic acids or vectors encoding the recombinant adenovirus) are administered in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, intratumoral or inhalation routes. The administration may be local or systemic. The compositions can be administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. Thus, the compositions are administered in a number of ways depending on whether local or systemic treatment is desired, and on the area to be treated.

In some embodiments, the compositions for administration will include a recombinant adenovirus (or recombinant genome) as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Pharmaceutical formulations, particularly, of the recombinant viruses can be prepared by mixing the recombinant adenovirus (or one or more nucleic acids encoding the recombinant adenovirus) having the desired degree of purity with optional pharmaceutically acceptable carriers, excipients or stabilizers. Such formulations can be lyophilized formulations or aqueous solutions.

Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives, low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants. The recombinant adenovirus (or one or more nucleic acids encoding the recombinant adenovirus) can be formulated at any appropriate concentration of infectious units.

Formulations suitable for oral administration can consist of (a) liquid solutions, such as an effective amount of the recombinant adenovirus suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The recombinant adenovirus (or one or more nucleic acids encoding the recombinant adenovirus), alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the provided methods, compositions can be administered, for example, by intravenous infusion, orally, topically, intraperitoneally, intravesically intratumorally, or intrathecally. Parenteral administration, intratumoral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced or infected by adenovirus or transfected with nucleic acids for ex vivo therapy can also be administered intravenously or parenterally as described above.

In some examples, the pharmaceutical preparation is in unit dosage form. In such form the preparation is subdivided into unit doses containing appropriate quantities of the active component. Thus, the pharmaceutical compositions can be administered in a variety of unit dosage forms depending upon the method of administration. For example, unit dosage forms suitable for oral administration include, but are not limited to, powder, tablets, pills, capsules and lozenges.

VII. Methods of Treatment

The recombinant adenoviruses, recombinant adenovirus genomes and compositions disclosed herein can be administered for therapeutic or prophylactic treatment. In particular, provided are methods of reducing or inhibiting tumor cell viability or growth in a subject, reducing or inhibiting tumor progression in a subject, reducing the number of metastases, reducing the size and/or volume of a metastasis, reducing tumor size and/or volume in a subject and/or treating cancer in a subject. The methods include administering a therapeutically effective amount of a recombinant adenovirus or recombinant adenovirus genome (or composition thereof) to the subject. As described throughout, the adenovirus or pharmaceutical composition is administered in any number of ways including, but not limited to, intravenously, intravascularly, intrathecally, intramuscularly, subcutaneously, intratumorally, intraperitoneally, or orally. Optionally, the method further comprising administering to the subject one or more additional therapeutic agents, such as a chemotherapeutic agent, biologic, and/or radiation.

In some embodiments, the cancer or tumor is a lung, prostate, colorectal, breast, thyroid, renal, pancreas, bone, head and neck, or liver cancer or tumor, or is a type of leukemia. In some cases, the cancer is metastatic. In some examples, the tumor is a tumor of the mammary, pituitary, thyroid, or prostate gland; a tumor of the brain, liver, meninges, bone, ovary, uterus, or cervix; monocytic or myelogenous leukemia; adenocarcinoma, adenoma, astrocytoma, bladder tumor, brain tumor, Burkitt's lymphoma, breast carcinoma, cervical carcinoma, colon carcinoma, kidney carcinoma, liver carcinoma, lung carcinoma, ovarian carcinoma, pancreatic carcinoma, prostate carcinoma, rectal carcinoma, skin carcinoma, stomach carcinoma, testis carcinoma, thyroid carcinoma, chondrosarcoma, choriocarcinoma, fibroma, fibrosarcoma, glioblastoma, glioma, hepatoma, histiocytoma, leiomyoblastoma, leiomyosarcoma, lymphoma, liposarcoma cell, mammary tumor, medulloblastoma, myeloma, plasmacytoma, neuroblastoma, neuroglioma, osteogenic sarcoma, pancreatic tumor, pituitary tumor, retinoblastoma, rhabdomyosarcoma, sarcoma, testicular tumor, thymoma, or Wilms tumor. Tumors include both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). In some aspects, solid tumors may be treated that arise from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, treatments may be useful in the prevention of metastases from the tumors described herein.

In therapeutic applications, recombinant adenoviruses or compositions thereof are administered to a subject in a therapeutically effective amount or dose. Amounts effective for this use will depend upon the severity of the disease and the general state of the patient's health. Single or multiple administrations of the compositions may be administered depending on the dosage and frequency as required and tolerated by the patient. A "patient" or "subject" includes both humans and other animals, particularly mammals. Thus, the methods are applicable to both human therapy and veterinary applications, such as mice, rats, rabbits, cats, dogs, cows, horses, pigs, chickens, and the like.

An effective amount of an adenovirus having a modified sequence is determined on an individual basis and is based, at least in part, on the particular recombinant adenovirus used; the individual's size, age, gender; and the size and other characteristics of the proliferating cells. For example, for treatment of a human, at least $10^3$ plaque forming units (PFU) of a recombinant virus is used, such as at least $10^4$, at least $10^5$, at least $10^6$, at least $10^7$, at least $10^8$, at least $10^9$, at least $10^{10}$, at least $10^{11}$, or at least $10^{12}$ PFU, for example approximately $10^3$ to $10^{12}$ PFU of a recombinant virus is used, depending on the type, size and number of proliferating cells or neoplasms present. The effective amount can be from about 1.0 pfu/kg body weight to about $10^{15}$ pfu/kg body weight (e.g., from about $10^2$ pfu/kg body weight to about $10^{13}$ pfu/kg body weight). A recombinant adenovirus is administered in a single dose or in multiple doses (e.g., two, three, four, six, or more doses). Multiple doses can be administered concurrently or consecutively (e.g., over a period of days or weeks).

In some embodiments, the provided methods include administering to the subject one or more additional therapeutic agents, such as an anti-cancer agent or other therapeutic treatment (such as surgical resection of the tumor).

Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens), anti-angiogenesis agents and CDK inhibitors. Other anti-cancer treatments include radiation therapy and other antibodies that specifically target cancer cells.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone).

Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

CDK (Cyclin-dependent kinase) inhibitors are agents that inhibit the function of CDKs. Non-limiting examples of CDK inhibitors for use in the provided methods include AG-024322, AT7519, AZD5438, flavopiridol, indisulam, P1446A-05, PD-0332991, and P276-00 (see e.g., Lapenna et al., Nature Reviews, 8:547-566, 2009). Other CDK inhibitors include LY2835219, Palbociclib, LEE011 (Novartis), pan-CDK inhibitor AT7519, seliciclib, CYC065. butyrolactone I, hyrnenialdisine, SU9516, CINK4, PD0183812 or fascaplysin.

In some examples, the CDK inhibitor is a broad-range inhibitor (such as flavopiridol, olomoucine, roscovitine, kenpaullone, SNS-032, AT7519, AG-024322, (S)-Roscovitine or R547). In other examples, the CDK inhibitor is a specific inhibitor (such as fascaplysin, ryuvidine, purvalanol A, NU2058, BML-259, SU 9516, PD0332991 or P-276-00).

In some embodiments, the provided methods further include administering to the subject a therapeutically effective amount of an immunotherapy. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech). The immunotherpautic agent can be a PD-1 antagonist or a PD-L1 antagonist, such as an antibody that specifically binds PD-1 or PD-L1, such as Atezolizumab, MPDL3280A, BNS-936558 (Nivolumab), Pembrolizumab, Pidilizumab, CT011, AMP-224, AMP-514, MEDI-0680, BMS-936559, BMS935559, MEDI-4736, MPDL-3280A, MSB-0010718C. The immunotherpautic agent can also be a CTLA-4, LAG-3, or B7-H3 antagonist, such as Tremelimumab, BMS-986016, and MGA271.

In some embodiments, the provided methods further include administering to the subject a therapeutically effective amount of one or more anti-angiogenic agents, such as proteins, enzymes, polysaccharides, oligonucleotides, DNA, RNA, and recombinant vectors, and small molecules that function to reduce or even inhibit blood vessel growth. Examples of suitable angiogenesis inhibitors include, without limitation, angiostatin K1-3, staurosporine, genistein, fumagillin, medroxyprogesterone, suramin, interferon-alpha, metalloproteinase inhibitors, platelet factor 4, somatostatin, thromobospondin, endostatin, thalidomide, and derivatives and analogs thereof. For example, in some embodiments the anti-angiogenesis agent is an antibody that specifically binds to VEGF (e.g., AVASTIN®, Roche) or a VEGF receptor (e.g., a VEGFR2 antibody). In one example the anti-angiogenic agent includes a VEGFR2 antibody, or DMXAA (also known as Vadimezan or ASA404; available commercially, e.g., from Sigma Corp., St. Louis, Mo.) or both. The anti-angiogenic agent can be bevacizumab, sunitinib, an anti-angiogenic tyrosine kinase inhibitors (TKI), such as sunitinib, xitinib and dasatinib. These can be used individually or in any combination.

In some embodiments, the provided methods further include administering to the subject a therapeutically effective amount of one or more kinase inhibitors, such as GLEEVAC®, IRESSA®, and TARCEVA®, sunitinib, sorafenib, anitinib, and dasatinib that prevent phosphorylation and activation of growth factors. Antibodies that can be used include HERCEPTIN® and AVASTIN® that block growth factors and the angiogenic pathway. These can be used individually or in combination.

In some embodiments, the provided methods further include administering to the subject a therapeutically effective amount of one or more therapeutic monoclonal antibodies, for example, 3F8, Abagovomab, Adecatumumab, Afutuzumab, Alacizumab, Alemtuzumab, Altumomab pentetate, Anatumomab mafenatox, Apolizumab, Arcitumomab, Bavituximab, Bectumomab, Belimumab, Besilesomab, Bev acizumab, Bivatuzumab mertansine, Blinatumomab, Brentuximab vedotin, Cantuzumab mertansine, Capromab pendetide, Catumaxomab, CC49, Cetuximab, Citatuzumab bogatox, Cixutumumab, Clivatuzumab tetraxetan, Conatumumab, Dacetuzumab, Detumomab, Ecromeximab, Eculizumab, Edrecolomab, Epratuzumab, Ertumaxomab, Etaracizumab, Farletuzumab, Figitumumab, Galiximab, Gemtuzumab ozogamicin, Girentuximab, Glembatumumab vedotin, Ibritumomab tiuxetan, Igovomab, Imciromab, Intetumumab, Inotuzumab ozogamicin, Ipilimumab, Iratumumab, Labetuzumab, Lexatumumab, Lintuzumab, Lorvotuzumab mertansine, Lucatumumab, Lumiliximab, Mapatumumab, Matuzumab, Mepolizumab, Metelimumab, Milatuzumab, Mitumomab, Morolimumab, Nacolomab tafenatox, Naptumomab estafenatox, Necitumumab, Nimotuzumab, Nofetumomab merpentan, Ofatumumab, Olaratumab, Oportuzumab monatox, Oregovomab, Panitumumab, Pemtumomab, Pertuzumab, Pintumomab, Pritumumab, Ramucirumab, Rilotumumab, Rituximab, Robatumumab, Satumomab pendetide, Sibrotuzumab, Sonepcizumab, Tacatuzumab tetraxetan, Taplitumomab paptox, Tenatumomab, TGN1412, Ticilimumab (tremelimumab), Tigatuzumab, TNX-650, Trastuzumab, Tremelimumab, Tucotuzumab celmoleukin, Veltuzumab, Volociximab, Votumumab, or Zalutumumab. In some examples, the heterologous ORF encodes one of these therapeutic antibodies.

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

The choice of agent and dosage can be determined readily by one of skill in the art based on the given disease being treated. Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions.

According to the methods disclosed herein, the subject is administered an effective amount of one or more of the agents provided herein. The effective amount is defined as any amount necessary to produce a desired physiologic response (e.g., killing of a cancer cell). Therapeutic agents are typically administered at the initial dosage of about 0.001 mg/kg to about 1000 mg/kg daily. A dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the subject, the severity of the condition being treated, and the compound being employed. For example, dosages can be empirically determined considering the type and stage of cancer diagnosed in a particular subject. The dose administered to a subject, in the context of the provided methods should be sufficient to affect a beneficial therapeutic response in the patient over time. Determination of the proper dosage for a particular situation is within the skill of the practitioner. Thus, effective amounts and schedules for administering the agent may be determined empirically by one skilled in the art. The dosage should not be so large as to cause substantial adverse side effects, such as unwanted cross-reactions, anaphylactic reactions, and the like. The dosage can be adjusted by the individual physician in the event of any contraindications. Guidance can be found in the literature for appropriate dosages for given classes of pharmaceutical products.

Provided herein is a method of inhibiting tumor cell viability or growth by contacting the tumor cell with a recombinant adenovirus, a recombinant adenovirus genome, or composition thereof, as disclosed herein. In some embodiments, the method is an in vitro method. In other embodiments, the method is an in vivo method and contacting the tumor cell comprises administering the recombinant adenovirus, recombinant adenovirus genome or composition to a subject with a tumor.

Further provided is a method of inhibiting tumor progression or reducing tumor volume in a subject, by administering to the subject a therapeutically effective amount of a recombinant adenovirus or recombinant adenovirus genome (or composition thereof) disclosed herein.

Also provided is a method of treating cancer in a subject, by administering to the subject a therapeutically effective amount of a recombinant adenovirus or recombinant adenovirus genome (or composition thereof) disclosed herein.

VIII. Adsembly and AdSLIC

The adenovirus genome is organized into several functional groups, labeled E1, E2, E3, E4, and L1-5. The E1 region encodes proteins that control the transcription of all other viral genes and induces S-phase in the host cell. The E2 region encodes proteins that drive viral DNA replication. The E3 region proteins modulate host cell immune response and are dispensable in cell culture. The E4 region contains genes for a disparate set of functions. And the L1-5 region encodes the viral particle structural proteins.

Figure 6A:
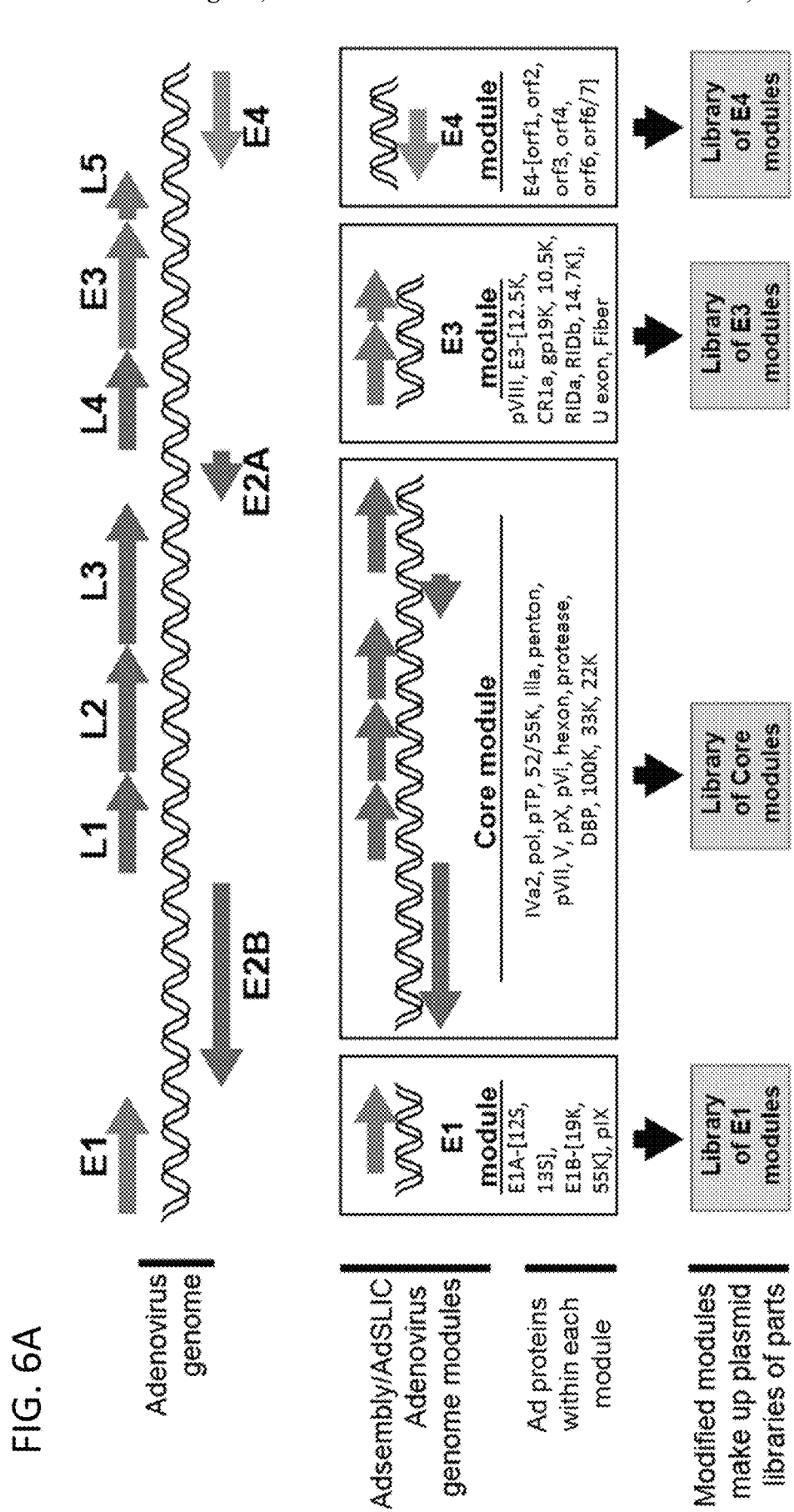
FIGS. 6A-6C provide a schematic overview of the Adsembly and AdSLIC techniques for the combinatorial assembly of recombinant adenoviruses.

Taking advantage of this natural segregation of functionality, the inventors previously developed a method of recombinant adenovirus assembly that allows quick and easy manipulation of the 36kb Ad genome by separating it into 4 plasmids, E1, E3, E4, and Core, as shown in FIG. 6A (Adsembly and AdSLIC; see WO 2012/024351, which is incorporated herein by reference). Because of their more reasonable size, manipulation of these smaller plasmids is straightforward using standard techniques.

Figure 6B:
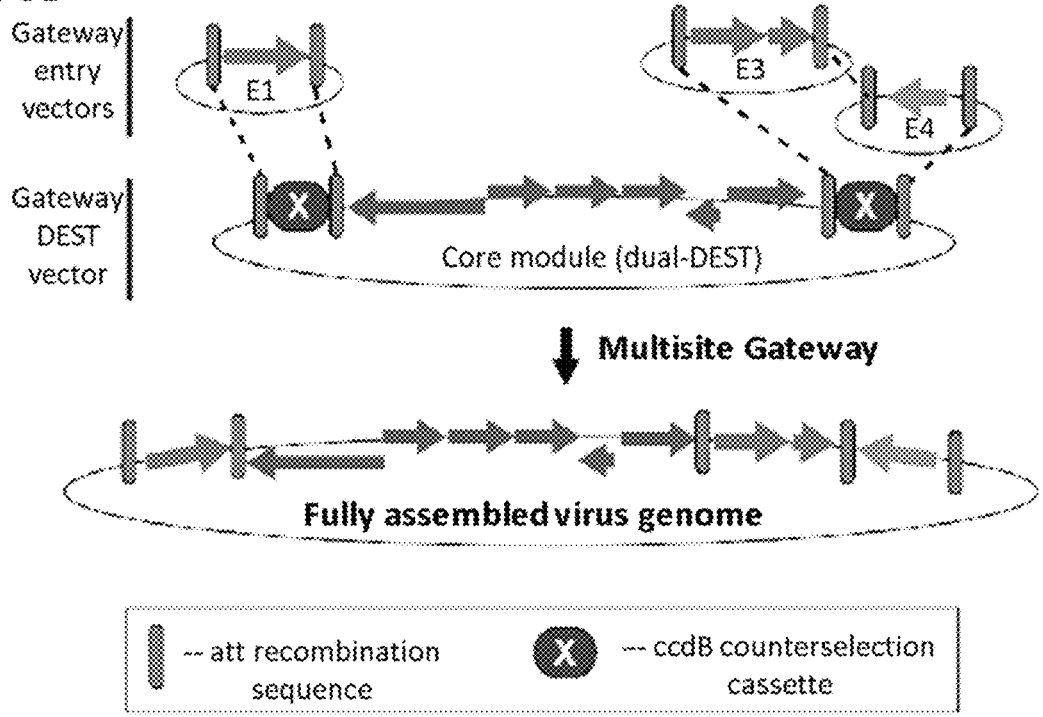
Figure 6C:
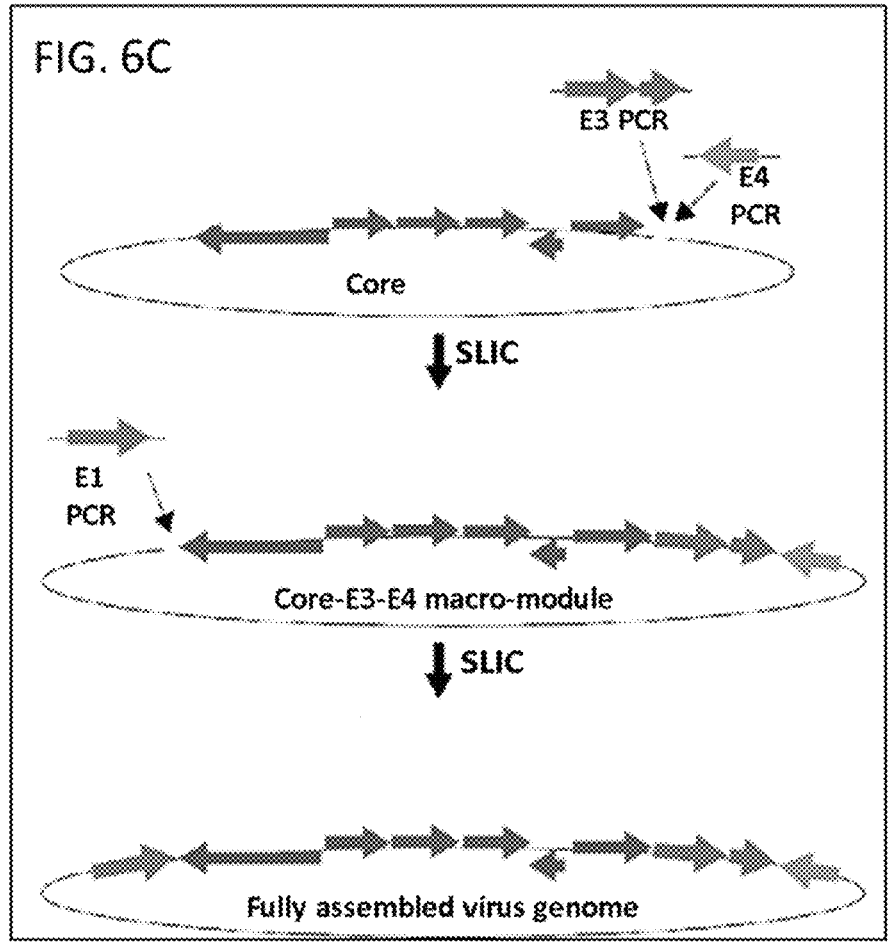

Adsembly and AdSLIC enable the combinatorial in vitro assembly of adenoviruses with novel properties from compatible genomic library parts in 4 hours. Adsembly and AdSLIC provide a common genome design platform that enables synthetic viruses with novel properties to be assembled using four libraries of functional parts (FIG. 6A). These libraries of parts can be re-assembled in all possible combinations using either multi-site specific recombination sites (Adsembly; FIG. 6B) or sequence independent seamless cloning (AdSLIC; FIG. 6C).

The Adsembly and AdSLIC technologies enable the modular design and production of adenoviruses with unique capabilities. Developing the capability to design, manufacture, and test viruses in an automated, high-throughput manner will accelerate and expand the development of new viruses for therapeutic, diagnostic, and research studies.

While the cloning step was once the bottleneck for producing new viral constructs, the advent of Adsembly and AdSLIC have made it such that the ability to construct viral genomes has outpaced the ability to test them. An equally high throughput kinetics assay is critical to exploit the full potential and high content assembly of synthetic and personalized viral therapies and diagnostics using the Adsembly and AdSLIC methods.

The following examples are provided to illustrate certain particular features and/or embodiments. These examples should not be construed to limit the disclosure to the particular features or embodiments described.

Examples

Example 1: Identification of Optimal Locations in the Adenovirus Genome for Exogenous ORFs This example describes the identification of specific locations within the adenovirus genome where exogenous ORFs can be inserted, along with a self-cleaving peptide sequence, without disrupting virus kinetics.

The insertion of exogenous genes in adenovirus vectors is limited by the size capacity of the adenovirus capsid. Excessive addition of exogenous nucleic acid leads to incomplete genome loading into the capsid and reduced viral kinetics. A solution to the challenge presented by the limited available space in the adenovirus genome is to locate exogenous open reading frames (ORFs) as fusion products within native adenovirus ORFs. This strategy makes use of adenovirus promoters, 5'UTRs, and polyA tails already encoded in the genome. However, expression of a fusion between a native adenovirus protein and an exogenous protein can be deleterious to one or both protein functions and lead to a significant decrease in adenovirus replication kinetics. In fact, studies disclosed herein demonstrate that direct fusion of an exogenous ORF to the adenovirus E1A, DNA polymerase or ADP ORFs significantly inhibits adenovirus replication kinetics. In addition, the inventors previously tried using an internal ribosomal entry site (IRES) to insert exogenous ORFs, which also failed to produce recombinant virus with wild-type kinetics.

This example describes a solution to this problem by using a self-cleaving peptide sequence placed between the native adenovirus ORF and the exogenous ORF. When placed between the two ORFs on a single mRNA, the presence of the self-cleaving peptide sequence leads to ribosome skipping and release of the first protein separate from the second protein. The adenovirus constructs generated in this example use the self-cleaving peptide P2A and a fluorescent protein (e.g. YPet, mCherry) as the heterologous ORF.

The table below provides a list of the constructs that were generated and indicates the expression level of the exogenous ORF (low, medium or high) and the level of virus replication kinetics (low, medium or high) in two different cells lines (293-E4 cells and A549 cells).

| Construct | Designation | SEQ ID NO: | Expression Level | Kinetics in 293-E4 cells | Kinetics in A549 cells |
|---|---|---|---|---|---|
| YPet-GS-E1A | CMBT-352 |  | Low | High | Low |
| YPet-P2A-E1A | CMBT-379 | 1 | High | High | Medium |
| E1A-P2A-YPet | CMBT-432 | 2 | Medium | High | Medium |
| E1A-P2A-YPet-PEST | CMBT-569 |  | Medium | High | Medium |
| E1A-P2A-mCherry | CMBT-455 |  | Medium | High | Medium |
| E1B-55k-P2A-YPet | CMBT-456 | 3 | High | High | High |
| E1B-55k-P2A-mCherry | CMBT-499 | 4 | High | High | High |
| YPet-P2A-(DNA Poly) | CMBT-530 | 5 | Medium | High | High |
| YPet-(DNA Poly) | CMBT-590 |  | Medium | None | Not tested |
| DBP-GS-BFP | CMBT-612 |  | High | High | Not tested |
| DBP-P2A-YPet | CMBT-886 | 6 | High | High | High |
| mCherry-GS-ADP | CMBT-402 |  | High | Medium | Not tested |
| ΔADP[mCherry] | CMBT-599 |  | High | High | Medium |
| YPet-P2A-ADP | CMBT-403 | 7 | High | High | High |
| ADP-P2A-YPet | CMBT-429 | 8 | High | Low | None |
| E3-14.7k-P2A-YPet | PCMN-887 | 9 | High | High | High |
| Fiber-GS-mCherry | CMBT-368 |  | High | Medium | None |
| Fiber-GS-tdTomato | CMBT-369 |  | High | None | Not tested |
| YPet-P2A-Fiber | CMBT-407 | 12 | High | None | Not tested |
| Fiber-P2A-YPet | CMBT-445 | 13 | Very High | Medium | None |
| Fiber-P2A-BFP | CMBT-632 |  | Very High | Medium | None |
| Fiber-GS-P2A-YPet | CMBT-446 |  | Very High | Medium | None |
| YPet-P2A-E4-ORF2 | CMBT-457 | 10 | Medium | High | High |
| mCherry-P2A-E4-ORF2 | CMBT-633 | 11 | Medium | High | High |

Constructs exhibiting "high" replication kinetics (i.e. replication kinetics that are comparable to wild-type adenovirus) in both cell types are considered candidates for generating therapeutic adenovirus constructs (show in bold). In addition, the fiber-P2A-heterologous ORF constructs exhibited significant defects in viral replication, but generated extraordinarily high levels of expression of the heterologous protein. Thus, these fiber constructs also can be used in therapeutic applications for production of high levels of a therapeutic protein in the context of a replication defective adenovirus.

Comparison of Direct Fusion and Insertion of a P2A Site

Several constructs were generated in which a fluorescent protein was fused directly to an adenovirus ORF. In particular, the following direct fusions were generated: YPet-E1A, YPet-(DNA polymerase) and mCherry-ADP.

YPet-E1A adenovirus exhibited a significant impairment in virus kinetics. Insertion of the P2A site between YPet and E1A (YPet-P2A-E1A) improved virus kinetics, but did not restore virus kinetics to wild-type level. Another construct was then generated to test fusion of P2A and YPet to the C-terminal end of E1A (E1A-P2A-YPet). This construct further improved virus kinetics, but again did not restore kinetics to the level of wild-type adenovirus.

Multiple attempts at transfecting the YPet-(DNA-poly) genome plasmid failed to produce viable virus (no plaques were formed). However, fusion of YPet-P2A to the N-terminus of DNA polymerase (YPet-P2A-(DNA poly)) produced a virus with wild-type kinetics, as shown in the table above.

In addition, the direct fusion of mCherry to ADP (mCherry-ADP) produced a virus with significantly impaired kinetics. However, insertion of the P2A site between the mCherry ORF and the ADP ORF resulted in a virus with wild-type kinetics (mCherry-P2A-ADP). The same result was obtained using a different fluorescent protein; the YPet-P2A-ADP construct exhibited wild-type virus kinetics. However, placement of P2A and the heterologous ORF on the C-terminal side of ADP produced a virus that did not replicate. Thus, for ADP, the heterologous ORF must be placed at the N-terminus.

Both direct fusion to fiber and insertion of a P2A site between fiber and a heterologous ORF produced viruses with significantly impaired replication kinetics. However, the recombinant adenoviruses comprising fiber-P2A-heterologous ORF exhibited extraordinarily high expression levels of the heterologous protein (YPet or blue fluorescent protein (BFP) in this example).

Additional Constructs with Wild-Type Virus Kinetics

Figure 7:
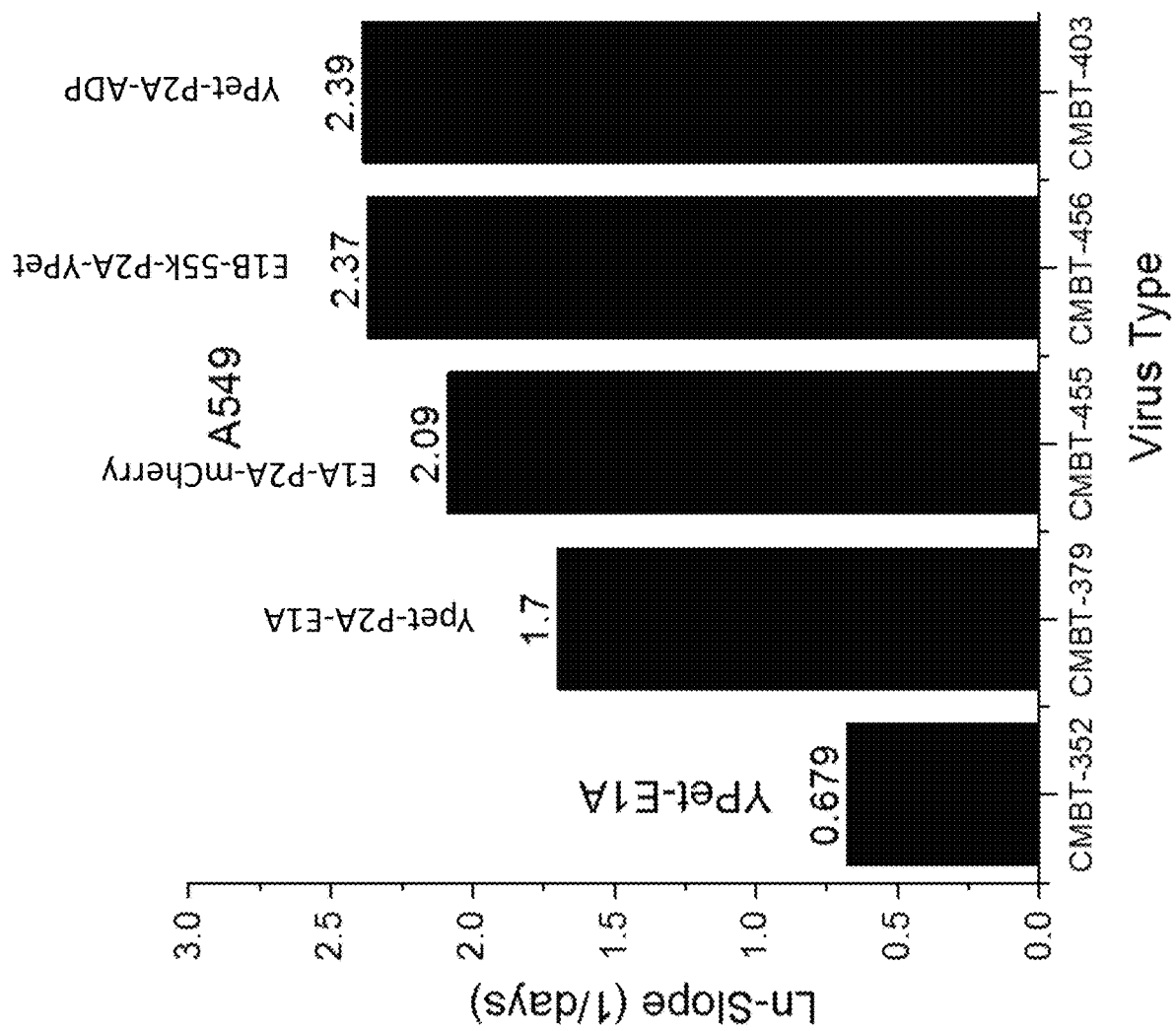
FIG. 7 is a bar graph showing ln-slope values for recombinant adenoviruses encoding a fluorescent protein in the E1 region. Shown are the values for the direct fusion construct YPet-E1A, and the YPet-P2A-E1A, E1A-P2A-mCherry and E1B-55k-P2A-YPet constructs, which each contain a P2A site. The YPet-P2A-ADP construct is shown for comparison.

FIG. 7 shows a comparison of Ln-Slope of six different constructs: YPet-E1A, YPet-P2A-E1A, E1A-P2A-mCherry, E1B-55k-P2A-YPet, YPet-P2A-ADP and Fiber-P2A-YPet. As discussed above, direct fusion of YPet to E1A produced a virus with significantly impaired kinetics, and addition of the P2A site at either the N-terminus (YPet-P2A-E1A) or the C-terminus (E1A-P2A-mCherry) improved virus kinetics but not to wild-type levels. However, inserting the P2A site and a heterologous ORF at the C-terminus of E1B-55k (E1B-55k-P2A-YPet) or the N-terminus of ADP (YPet-P2A-ADP) generated a recombinant virus with wild-type virus kinetics.

Evaluation of viral kinetics for constructs having a P2A site and heterologous ORF on the C-terminus of DBP (DBP-P2A-YPet) or the C-terminus of E3-14.7k (E3-14.7k-P2A-YPet), or having a P2A site and heterologous ORF on the N-terminus of E4-ORF2 (YPet-P2A-E4-ORF2 and mCherry-P2A-E4-ORF2) produced viruses with wild-type replication kinetics.

The results of these data demonstrate that at least the following adenovirus genome constructs can be used to develop therapeutic adenovirus constructs:
E1B-55k-P2A-heterologous ORF
heterologous ORF-P2A-(DNA polymerase)
DBP-SC-heterologous ORF
heterologous ORF-SC-ADP
E3-14.7k-SC-heterologous ORF
heterologous ORF-P2A-E4-ORF2
fiber-P2A-heterologous ORF For therapeutic applications, the heterologous ORF encodes a therapeutic protein.

Other Adenovirus Serotypes

Figure 9B:
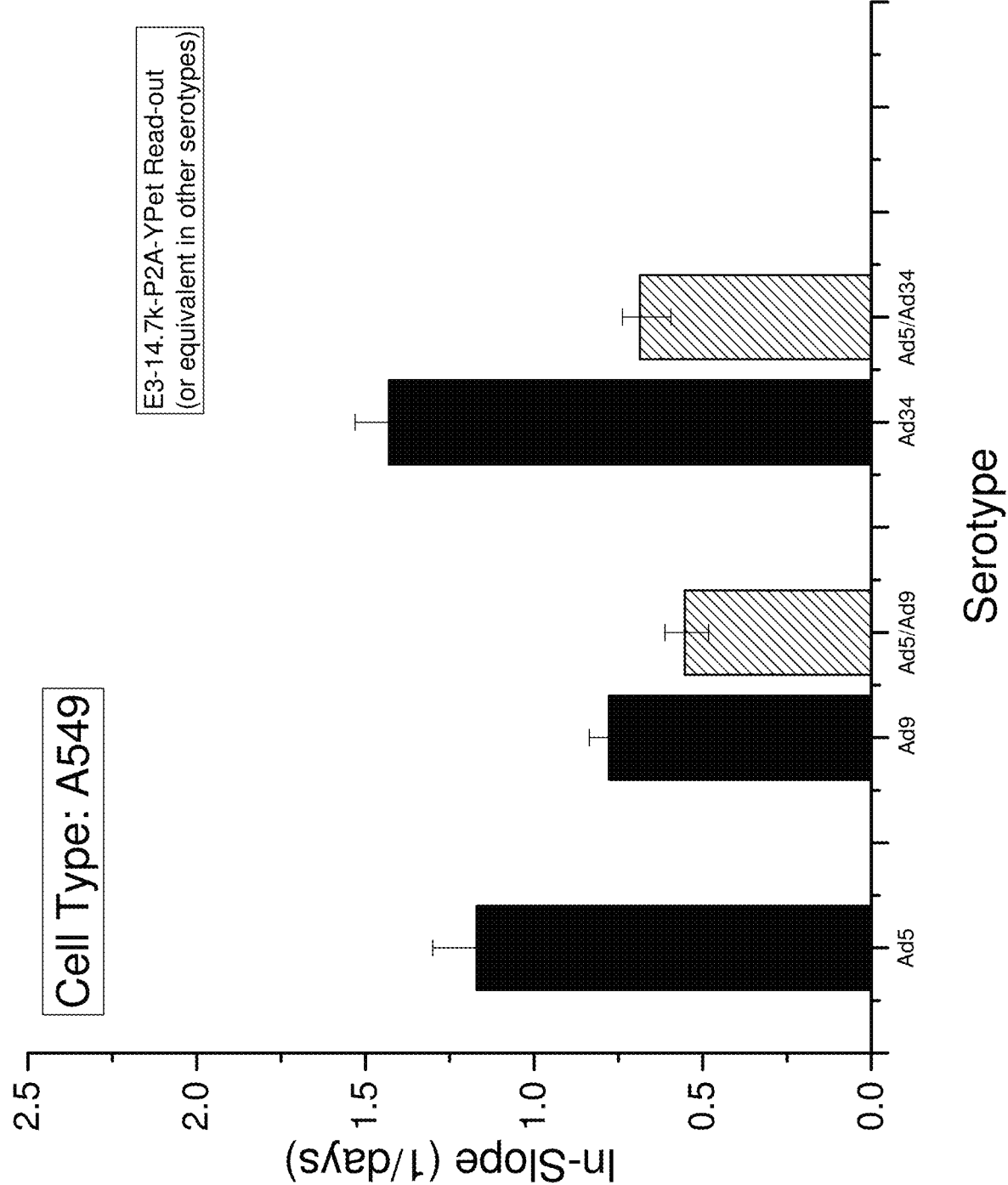
Figure 9C:
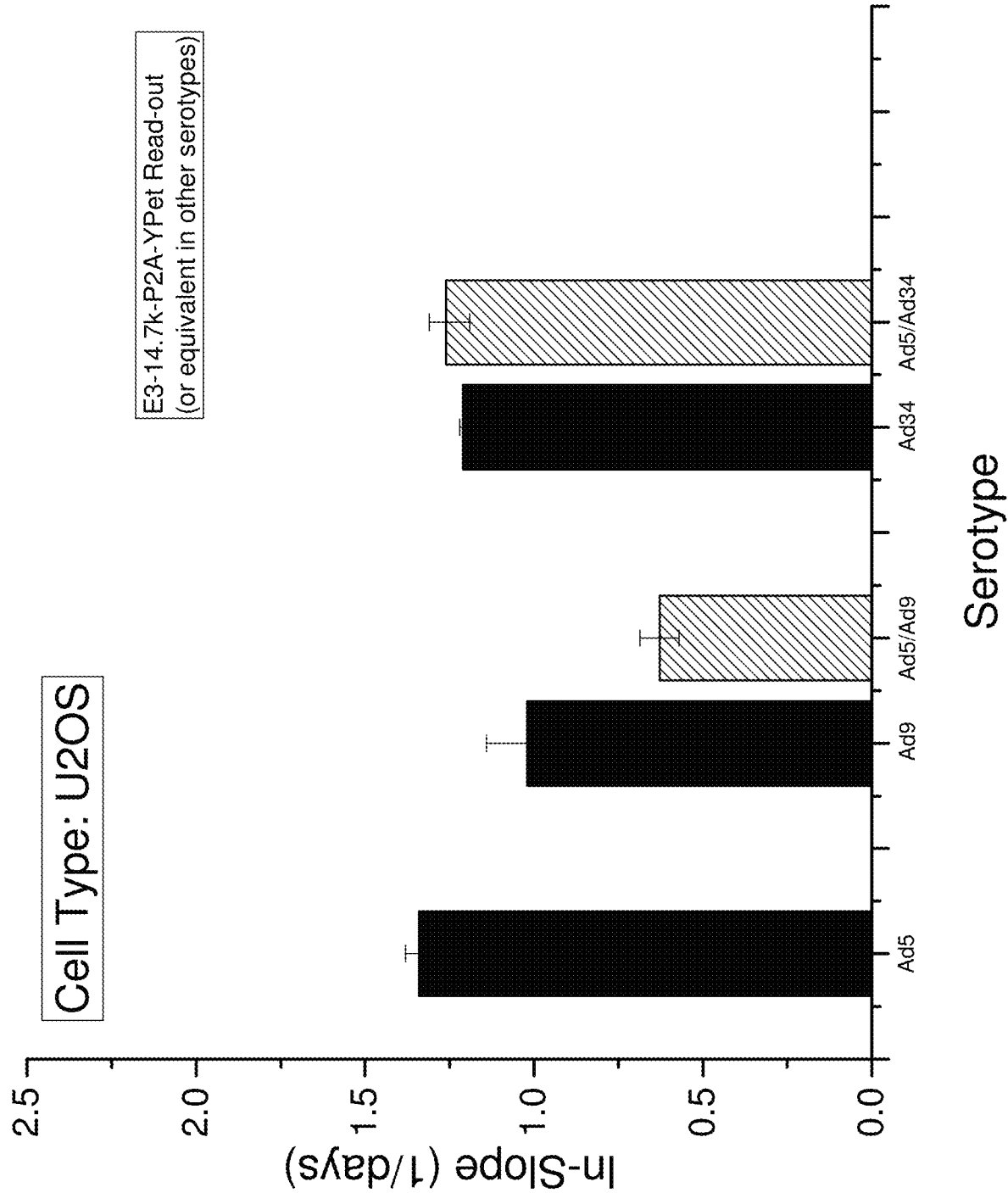

Previously described methods of measuring viral kinetics are all highly dependent upon cell-type specific assays and are thus serotype specific due to the divergent tropism of each adenovirus serotype. The adenovirus kinetic assay disclosed herein is not dependent upon any one cell type and so can be extended to serotypes other than Ad5. All adenovirus serotypes contain an ORF equivalent to Ad5 E3-14.7k. Therefore, viruses equivalent to Ad5 E3-14.7k-P2A-YPet (PCMN-887; SEQ ID NO: 9) were generated using Ad9 (containing E3-15k) and Ad34 (containing E3-14.8k): PCMN-888 (Ad9 E3-15k-P2A-YPet; SEQ ID NO: 22) and PCMN-889 (Ad34 E3-14.8k-P2A-YPet; SEQ ID NO: 23). Chimeric viruses containing the Ad5 core and a fiber shaft and knob from either Ad9 or Ad34 were also generated. The four recombinant viruses were then tested in the FBVK assay using 293 cells (FIG. 9A), A549 cells (FIG. 9B) and U2OS cells (FIG. 9C). All four recombinant viruses exhibited high levels of YPet expression with minimal impact on viral kinetics resulting from insertion of the exogenous ORF.

Example 2: Methods for Evaluating Adenovirus Replication Kinetics

The Adsembly and AdSLIC methods for assembling recombinant adenoviruses provide a means for generating large numbers of recombinant virus genomes and viruses in a short period of time. However, a need exists for a rapid and high-throughput method for evaluating replication kinetics of recombinant adenoviruses designed for clinical and therapeutic use. This example describes a fluorescence-based viral kinetics assay that can be used to test virus replication kinetics of recombinant adenoviruses (FIG. 3). The assay can be performed with either recombinant adenovirus genome plasmids or recombinant adenovirus particles as the starting material.

When starting with a recombinant adenovirus genome, the assay includes transfecting cells with adenovirus genome plasmids (such as those described above in Example 1) and monitoring fluorophore expression over time (FIGS. 4A-4B). Transfection conditions are selected such that about 5-10% of the cells are initially transfected. Cells that are not initially transfected are available for secondary infection by virus particles produced from the initial transfection. Log-slope is used as a measure of kinetics based on secondary, tertiary, and quarternary (etc.) infections, thus it is not necessary to know the percentage of cells that are initially transfected. FIGS. 4A and 4B show an exemplary virus-based kinetics assay starting with recombinant adenovirus genome plasmids. In this example, a 48-well plate is used, which allows for testing of 14 different virus constructs (in triplicate) simultaneously. The upper half of the 48-well plate (FIG. 4A) includes triplicate wells of six different viruses, 3 mock-infected wells and 3 "blank" wells with FLUORESBRITE™ beads, which compensate for tool sensitivity drift. The lower half of the 48-well plate (FIG. 4B) includes triplicate wells of eight different virus constructs. Once cells are transfected, the plate is placed in a TECAN™ plate reader for continuous fluorescence monitoring. The data collected is used to calculate ln-slope for each construct (FIG. 8).

Figure 5:
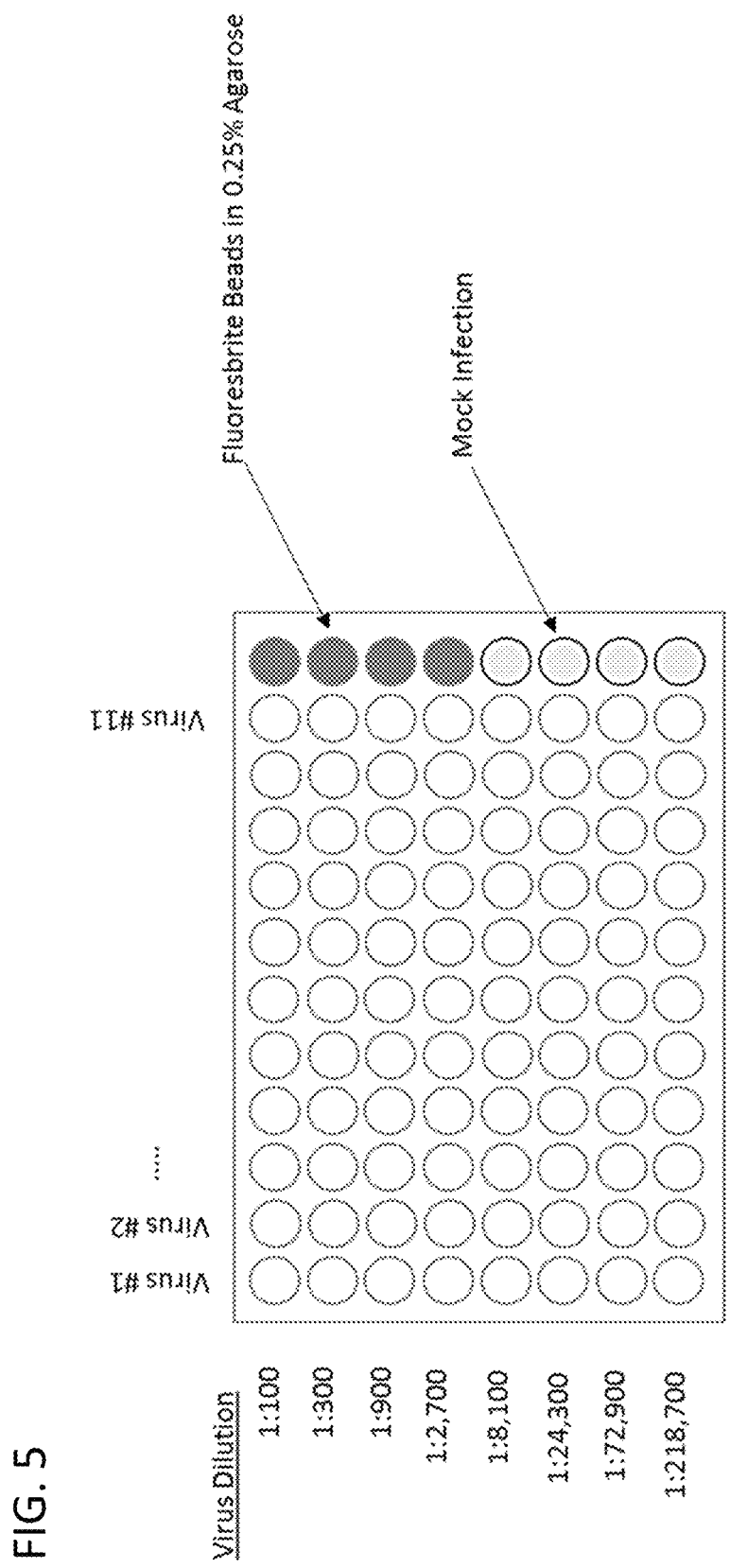
FIG. 5 outlines the kinetic assay setup when starting with recombinant virus. This assay does not require accurate knowledge of virus titer. Recombinant virus is serially diluted and used to infect cells plated in a multi-well plate. In the example shown, a 96-well plate is used and each virus is diluted 1:100, 1:300, 1:900, 1:2700, 1:8100, 1:24,300, 1:72,900 and 1:218,700, allowing for the testing of 11 viruses simultaneously. Four wells are mock-infected and FLUORESBRITE™ beads are placed in four wells to compensate for tool sensitivity and drift. The multi-well plate is placed on a plate reader (such as a TECAN plate reader) for continuous fluorescence monitoring.

The assay can also be carried out by infecting cells with recombinant virus particles. In this version of the assay, cells are infected with recombinant virus particles and fluorophore expression is monitored over time (FIG. 5). As with the genome plasmid version of the assay, it is not necessary to know the exact titer of the starting virus stock. Typically, a dilution series is used for initial infection, such as a dilution series ranging from 1:100 to 1:218,700, as shown in FIG. 5. A dilution of 1:100 generally leads to infection of all cells, whereas a dilution of 1:218,700 generally leads to initial infection of very few cells. In this example, a 96-well plate is used and 11 different virus constructs are tested simultaneously at eight different dilutions (1:100, 1:300, 1:900, 1:2700, 1:8100, 1:24,300, 1:72,900 and 1:218,700). The plate also includes four wells of mock-infected cells and four wells of FLUORESBRITE™ beads. Once the cells are infected, the plate is placed in a TECAN™ plate reader for continuous fluorescence monitoring. The data collected is used to calculate ln-slope for each construct (FIG. 8).

The TECAN™ plate readers also provide incubation functions (maintaining an appropriate temperature as well as $CO_2$ and $O_2$ levels). Data points are taken every 15 minutes to calculate the ln-slope. Using these methods, it is possible to rapidly and efficiently compare the kinetics between a number of different viruses and between different cell types. For example, to evaluate whether particular recombinant adenoviruses could be used therapeutically as oncolytic viruses, this assay could be employed to find viruses that exhibit high replication kinetics in tumor cells, but slow virus kinetics in non-tumor cells. Furthermore, the virus kinetics of the recombinant viruses can be evaluated by infecting or transfecting the tumor cell type of interest in this assay.

Calculating Log-Slope

To measure log-slope, the linear plot of fluorescence intensity versus time is converted to a semi-log plot by taking the natural logarithm of the measured fluorescence intensity at each time point. Since the fluorescence intensity exhibits exponential growth during viral replication, this conversion results in a straight line when plotting ln(fluorescence intensity) vs. time. This straight line is then fit using standard least-squares methods. The resulting slope produced by this fit is the ln-slope of the fluorescence vs. time and thus the ln-slope of the viral growth vs. time. Equations are shown below.

$FI(t) = F_0 e^{\alpha(t-t_0)}$; where FI is measured fluorescence intensity, t is time, $F_0$ is the initial fluorescence intensity at time=$t_0$, and $\alpha$ is the ln-slope.

Take natural logarithm of both sides:

$$\ln[FI(t)] = \ln[F_0 e^{\alpha(t-t_0)}] = \ln(F_0) + \alpha(t-t_0)$$

The right hand side is now a linear equation with a ln-slope of $\alpha$.

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10738325B2). An electronic copy of the "Sequence Listing" will also be available from the USPTO upon request and payment of the fee set forth in 37 CFR 1.19(b)(3).

The invention claimed is:

1. A recombinant adenovirus genome, comprising a heterologous open reading frame (ORF) and a self-cleaving peptide coding sequence, both operably linked to and in the same reading frame as an endogenous adenovirus ORF, wherein the self-cleaving peptide coding sequence is located between the heterologous ORF and the endogenous ORF, and wherein:
   the endogenous ORF is E1B-55k and the heterologous ORF is 3' of E1B-55k;
   the endogenous ORF is DNA polymerase and the heterologous ORF is 5' of DNA polymerase;
   the endogenous ORF is DNA-binding protein (DBP) and the heterologous ORF is 3' of DBP;
   the endogenous ORF is adenovirus death protein (ADP) and the heterologous ORF is 5' of ADP;
   the endogenous ORF is E3-14.7k and the heterologous ORF is 3' of E3-14.7k;
   the endogenous ORF is E4-ORF2 and the heterologous ORF is 5' of E4-ORF2; or
   the endogenous ORF is fiber and the heterologous ORF is 3' of fiber,
   wherein the heterologous ORF encodes a therapeutic protein.

2. The recombinant adenovirus genome of claim 1, wherein the therapeutic protein comprises an immunomodulator.

3. The recombinant adenovirus genome of claim 1, wherein the self-cleaving peptide is a 2A peptide or variant thereof.

4. The recombinant adenovirus genome of claim 3, wherein the 2A peptide comprises a porcine teschovirus-1 (PTV1) 2A (P2A) peptide, a foot and mouth disease virus (FMDV) 2A (F2A) peptide, an equine rhinitis A virus (ERAV) 2A (E2A) peptide or a Thosea asigna virus (TaV) 2A (T2A) peptide, or a variant thereof.

5. The recombinant adenovirus genome of claim 4, wherein the amino acid sequence of the self-cleaving peptide is at least 80% identical to the amino acid sequence of any one of SEQ ID NOs: 14-21.

6. The recombinant adenovirus genome of claim 4, wherein the self-cleaving peptide comprises the amino acid sequence of any one of SEQ ID NOs: 14-21.

7. A composition comprising the recombinant adenovirus genome of claim 1 and a pharmaceutically acceptable carrier.

8. A recombinant adenovirus comprising the recombinant adenovirus genome of claim 1.

9. A composition comprising the recombinant adenovirus of claim 8 and a pharmaceutically acceptable carrier.

10. A method of delivering a therapeutic protein to a subject, comprising administering to the subject the recombinant adenovirus of claim 8.

11. A method of inhibiting tumor cell viability and/or tumor cell growth, comprising contacting the tumor cell with the recombinant adenovirus of claim 8.

12. The method of claim 11, wherein the method is an in vitro method.

13. The method of claim 11, wherein the method is an in vivo method and contacting the tumor cell comprises administering the recombinant adenovirus genome, recombinant adenovirus, or composition to a subject with a tumor.

14. A method of inhibiting tumor progression or reducing tumor volume in a subject, comprising administering to the subject a therapeutically effective amount of the recombinant adenovirus of claim 8, thereby inhibiting tumor progression or reducing tumor volume in the subject.

15. A method of treating cancer in a subject, comprising administering to the subject a therapeutically effective amount of the recombinant adenovirus of claim 8, thereby treating cancer in the subject.

16. The method of claim 15, further comprising administering an additional therapeutic agent to the subject.

17. A kit comprising:
   (i) the recombinant adenovirus genome of claim 1; and
   (ii) one or more additional therapeutic agents and/or one or more diagnostic agents.

18. The kit of claim 17, wherein the one or more additional therapeutic agents comprise a chemotherapeutic, a biologic, or a combination thereof.

19. The kit of claim 17, wherein the one or more diagnostic agents comprise one or more antibodies that bind a tumor marker.

20. The recombinant adenovirus genome of claim 4, wherein the amino acid sequence of the self-cleaving peptide is at least 90% identical to the amino acid sequence of any one of SEQ ID NOs: 14-21.

* * * * *